(12) United States Patent
Schnabel et al.

(10) Patent No.: US 11,549,148 B2
(45) Date of Patent: Jan. 10, 2023

(54) NEUROENDOCRINE TUMORS

(71) Applicant: BIOTHERANOSTICS, INC., San Diego, CA (US)

(72) Inventors: Catherine A. Schnabel, San Diego, CA (US); Yi Zhang, San Diego, CA (US); Mark G. Erlander, Carlsbad, CA (US)

(73) Assignee: BIOTHERANOSTICS, INC., San Diego, CA (US)

( * ) Notice: Subject to any disclaimer, the term of this patent is extended or adjusted under 35 U.S.C. 154(b) by 0 days.

(21) Appl. No.: 15/656,998

(22) Filed: Jul. 21, 2017

(65) Prior Publication Data

US 2018/0135131 A1 May 17, 2018

Related U.S. Application Data

(63) Continuation of application No. 14/223,473, filed on Mar. 24, 2014, now abandoned.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 6,328,709 B1 | 12/2001 | Hung et al. | |
| 7,364,846 B2 | 4/2008 | Erlander et al. | |
| 9,670,553 B2 * | 6/2017 | Erlander | C12Q 1/6886 |
| 2006/0019256 A1 | 1/2006 | Clarke et al. | |
| 2006/0094035 A1 | 5/2006 | Erlander et al. | |
| 2007/0020655 A1 | 1/2007 | Erlander et al. | |
| 2012/0258442 A1 * | 10/2012 | Erlander | C12Q 1/6886 |
| | | | 435/5 |

FOREIGN PATENT DOCUMENTS

| | | |
|---|---|---|
| WO | WO 2011/116380 A2 | 9/2011 |
| WO | WO 2013/002750 A2 | 1/2013 |

OTHER PUBLICATIONS

Kerr (Modern Pathology, 2014, 27:44-54).*
Yalcin (Cancer Treatment Review, 2011, 37, pp. 127-132).*
Ma et al., "Molecular classification of human cancers using a 92-gene real-time quantitative polymerase chain reaction assay", Arch Pathol Lab Med., 130(4):465-473 (2006).
Jones et al., "Two prognostically significant subtypes of high-grade lung neuroendocrine tumours independent of small-cell and large-cell neuroendocrine carcinomas identified by gene expression profiles", Lancet, 363(9411):775-791 (2004).
Altschul et al., "Basic Local Alignment Search Tool," *J. Mol. Biol.*, 215:403-410 (1990).
Bobos et al., "Immunohistochemical distinction between merkel cell carcinoma and small cell carcinoma of the lung," *Am. J. Dermatopathol.*, 28(2):99-104 (2006).
Cheuk et al., "Immunostaining for thyroid transcription factor 1 and cytokeratin 20 aids the distinction of small cell carcinoma from Merkel cell carcinoma, but not pulmonary from extrapulmonary small cell carcinomas," *Arch. Pathol. Lab Med*, 125(2):228-231 (2001).
Klimstra et al., "The pathologic classification of neuroendocrine tumors: a review of nomenclature, grading, and staging systems," *Pancreas*, 39(6):707-712 (2010).
Sangoi et al., "PAX8 expression reliably distinguishes pancreatic well-differentiated neuroendocrine tumors from ileal and pulmonary well-differentiated neuroendocrine tumors and pancreatic acinar cell carcinoma," *Mod. Pathol.*, 24(3): 412-424 (2011).
Scarpa et al., "Pancreatic endocrine tumors: improved TNM staging and histopathological grading permit a clinically efficient prognostic stratification of patients," *Mod. Pathol.*, 23(6):824-833 (2010).
Srivastava et al., "Immunohistochemical staining for CDX-2, PDX-1, NESP-55, and TTF-1 can help distinguish gastrointestinal carcinoid tumors from pancreatic endocrine and pulmonary carcinoid tumors," *Am. J. Surg. Pathol.*, 33(4):626-632 (2009).
Zuetenhorst et al., "Metastatic carcinoid tumors: a clinical review," *Oncologist*, 10(2):123-131 (2005).

* cited by examiner

*Primary Examiner* — Sarae L Bausch
(74) *Attorney, Agent, or Firm* — Finnegan, Henderson, Farabow, Garrett & Dunner, LLP; Michael J. Gilly

(57) ABSTRACT

The disclosure provides methods for the use of gene expression measurements to classify or identify neuroendocrine cancer in samples obtained from a subject in a clinical setting, such as in cases of formalin fixed, paraffin embedded (FFPE) samples.

10 Claims, 8 Drawing Sheets
Specification includes a Sequence Listing.

| GENE SYMBOL | ALTERNATE NAMES | LOCATION | GENE FUNCTION | AUC |
|---|---|---|---|---|
| ELAVL4 | EMBRYONIC LETHAL ABNORMAL VISION DROSOPHILA-LIKE 4, HU ANTIGEN D (HUD), PARANEOPLASTIC ENCEPHALOMYELITIS ANTIGEN (PNEM) | 1p34 | ONCO-NEURAL RNA BINDING PROTEIN, ANTI-HU ANTIBODIES HAVE BEEN ASSOCIATED WITH PARANEOPLASTIC ENCEPHALOMYELITIS AND SENSORY NEUROPATHY, MAY BE INVOLVED IN THE ONSET OF NEUROENDOCRINE TUMORS, ESPECIALLY NON-SMALL CELL LUNG CANCER. EXPRESSED IN PANCREATIC BETA CELLS AND MAY INVOVLE IN INSULIN REGULATION 74-76. | 0.97 |
| CADPS | CALCIUM DEPENDENT SECRETION ACTIVATOR, CAPS, CAPS1, CADPS1 | 3p14.2 | PROTEIN REQUIRED FOR CALCIUM REGULATED EXOCYTOSIS OF NEUROSECRETORY VESICLES 76. | 0.94 |
| RGS17 | REGULATOR OF G-PROTEIN SIGNALING 17, RGSZ2 | 6q25.3 | ENCODES PROTEIN IN FAMILY OF REGULATORS OF G-PROTEIN SIGNALING, OVEREXPRESSED IN A VARIETY OF HUMAN CANCERS 77-79. | 0.91 |
| KCNJ11 | POTASSIUM INWARDLY-RECTIFYING CHANNEL SUBFAMILY J MEMBER 11, BIR, HHF2, PHHI, IKATP, TNDM3, KIR6.2 | 11p15.1 | POTASSIUM CHANNEL, MUTATIONS CAUSE FAMILIAL PERSISTENT HYPERINSULINEMIC HYPOGLYCEMIA OF INFANCY AND MAY CONTRIBUTE TO OTHER DISORDERS OF INSULIN SECRETION 80-82. | 0.83 |

FIG. 2A

NEUROENDOCRINE TUMORS

RELATED APPLICATIONS

This application is a continuation of U.S. application Ser. No. 14/223,473, filed Mar. 24, 2014, the entire content of which is incorporated by reference herein in its entirety as if fully set forth.

FIELD OF THE DISCLOSURE

This disclosure relates to the use of gene expression to classify neuroendocrine tumors. The classification is performed by use of gene expression profiles, or patterns, of expressed sequences as disclosed herein. The expression levels of the sequences are expressed in patterns that permit the classification of neuroendocrine tumors even though expression occurs in more than one type of tumor. The gene expression profiles, whether embodied in nucleic acid expression, protein expression, or other expression formats, may be used to classify a cell containing sample of neuroendocrine tumor cells. This permits a more accurate identification of neuroendocrine cancer, treatment of the cancer, and determination of the prognosis of the subject from whom the sample was obtained.

BACKGROUND OF THE DISCLOSURE

This disclosure relates to cancers of unknown origin, or carcinoma of unknown primary (CUP). These terms refer to a disease where malignant cancer cells are found in tissue where the malignant cells did not originate. The terms also refer to condition of metastasized cancer cells in a tissue, such as that of a human patient, but the place the cancer began is not known.

Cancer can occur in any tissue of a body with multiple organ types and can form a primary tumor. Cells from a first formed primary tumor can re-locate to other tissues in a body through a process called metastasis. Metastasized cancer cells may look like the cells in the tissue from which the cancer originated. As an example, breast cancer cells that have spread to lung tissue appear similar to cells in a primary breast cancer tumor because the cancer began in the breast.

When metastasized cancer is detected without knowledge of the tissue where the cancer first began to grow, the metastasized cancer is called a cancer (or carcinoma) of unknown primary (CUP) or occult primary tumor.

Neuroendocrine neoplasia occurs in a variety of organ sites and tissue types. But where neuroendocrine tumors are present in a location distinct from the site of origin, they can provide a diagnostic challenge because clinical context is lacking. Identifying the site of origin for neuroendocrine tumors has become increasingly important (see for example, Klimstra et al. 2010 "The pathologic classification of neuroendocrine tumors: a review of nomenclature, grading, and staging systems." *Pancreas* 39(6): 707-712; and Scarpa et al. 2010 "Pancreatic endocrine tumors: improved TNM staging and histopathological grading permit a clinically efficient prognostic stratification of patients." *Mod Pathol.* 23(6): 824-833).

The subtyping of neuroendocrine tumors is also important (see for example, Cheuk et al. 2001 "Immunostaining for thyroid transcription factor 1 and cytokeratin 20 aids the distinction of small cell carcinoma from Merkel cell carcinoma, but not pulmonary from extrapulmonary small cell carcinomas." *Arch Pathol Lab Med.* 125(2): 228-231; Bobos et al. 2006 "Immunohistochemical distinction between merkel cell carcinoma and small cell carcinoma of the lung." *Am J Dermatopathol.* 28(2): 99-104; Srivastava et al. 2009 "Immunohistochemical staining for CDX-2, PDX-1, NESP-55, and TTF-1 can help distinguish gastrointestinal carcinoid tumors from pancreatic endocrine and pulmonary carcinoid tumors." *Am J Surg Pathol.* 33(4): 626-632; and Sangoi et al. 2011 "PAX8 expression reliably distinguishes pancreatic well-differentiated neuroendocrine tumors from ileal and pulmonary well-differentiated neuroendocrine tumors and pancreatic acinar cell carcinoma." *Mod Pathol.* 24(3): 412-424).

A panel of immunohistochemical stains (CDX-2, PDX-1, NESP-55, TTF-1, PAX8) has been proposed to distinguish between gastrointestinal, pancreatic, and pulmonary carcinoid tumors. But this approach appears to have relatively low sensitivities. Additionally, unknown primary sites are estimated to occur in up to 10% of cases of well-differentiated neuroendocrine tumors (Zuetenhorst et al. 2005 "Metastatic carcinoid tumors: a clinical review." *Oncologist* 10(2): 123-131).

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

BRIEF SUMMARY OF THE DISCLOSURE

This disclosure relates to the use of gene expression measurements to classify or identify unknown, or occult, cancers and/or tumors in cell containing samples obtained from a subject in a clinical setting. This disclosure features classification or identification of a sample of a neuroendocrine tumor or neuroendocrine carcinoma (NEC). The samples may be formalin fixed, paraffin embedded (FFPE) samples as well as fresh samples, such as samples that have undergone no treatment to little or minimal treatment (such as simply storage at a reduced, non-freezing, temperature), and frozen samples. The disclosure thus provides the ability to classify a sample under real-world conditions faced by hospital and other laboratories which conduct testing on clinical FFPE samples. The samples may be of a primary tumor sample or of a tumor that has resulted from metastasis. Alternatively, the sample may be a cytological sample, such as, but not limited to, cells in a blood sample or other bodily fluid. The disclosure may also be viewed as molecular profiling of an unknown cancer or tumor by predicting tissue of origin for the cancer or tumor.

The determination of a neuroendocrine carcinoma (NEC) may be straight-forward in some circumstances, such as by use of morphological criteria. But in other cases, the tumor site of origin may remain unknown or uncertain, such as in a case of metastatic presentation. This disclosure may be applied to both situations as described herein. As non-limiting examples, a tumor sample may not have undergone classification by traditional pathology techniques, may have been initially classified but confirmation is desired, or have been classified as a "carcinoma of unknown primary" (CUP) or "tumor of unknown origin" (TUO) or "unknown primary tumor". This disclosure further provides means for cancer identification, or CID, of a tumor or tumor sample as being a subtype of neuroendocrine tumor or NEC.

In a first aspect of the disclosure, the classification, identification, or subtyping is performed by use of gene expression profiles, or patterns, of expressed sequences disclosed herein. The gene expression profiles, whether embodied in nucleic acid expression, protein expression, or other markers of gene expression, may be used to determine a cell containing sample as containing a subtype of neuroendocrine tumor cells. This permits a more accurate identification of the cancer as well as staging and patient management. Additionally, determining treatment and the prognosis of the subject, from whom the sample was obtained, may be based upon the classification, identification, or subtype.

The expression products of the expressed sequences may be found in multiple tumor types within a plurality, or group, of known possible tumor types. The expression levels of the sequences may thus occur in more than one tumor type. Additionally, the range of expression levels may overlap between known tumor types. The disclosed methodology of classifying or identifying tumor types may also be applied to the classification or identification of a tissue source of a neuroendocrine tumor cell.

In some embodiments the disclosure provides for the classifying of a cell containing sample as containing a subtype of neuroendocrine tumor based on gene expression of disclosed sequences. In some cases, the subtype is selected from adrenal-pheochromocytoma or paraganglioma, gastrointestinal neuroendocrine tumor (or neuroendocrine tumors from the alimentary tract such as, but not limited to, carcinoids and high grade neuroendocrine carcinomas from the stomach, small intestine, appendix, and colorectum), pulmonary (lung) carcinoid (or low grade lung cancer), neuroendocrine lung-small cell and lung-large cell (including pulmonary small cell carcinoma or large cell neuroendocrine carcinoma), pancreatic neuroendocrine tumor (or pancreatic endocrine tumor), Merkel cell carcinoma (or neuroendocrine tumor of the skin), and medullary thyroid carcinoma.

The classification or identification may be performed by the comparison of gene expression profiles, or patterns, of disclosed sequences in a tumor sample to the expression of the same expressed sequences in a plurality of known neuroendocrine tumor specimens.

In other embodiments, the disclosure is used to identify neuroendocrine tumor cells from among a group of multiple (such as up to 54 or more) known tumor or cancer types as a plurality. The classification may be performed with significant accuracy in a clinical setting.

In another aspect, the disclosure provides for the classifying of a cell containing sample as containing a subtype of neuroendocrine tumor cell by determining the expression levels of 2 or more, 3 or more, 4 or more, 6 or more, 7 or more, 8 or more, 9 or more, 10 or more, 11 or more, 12 or more, 13 or more, 14 or more, or all 15 disclosed sequences and comparing the expression levels to that of the same transcribed sequences in a plurality or group of known neuroendocrine tumor subtypes to classify the cell containing sample as containing a neuroendocrine cancer (or tumor) cell of a subtype among the plurality of subtypes.

In a further aspect, the disclosure includes a kit for use with a sample of tumor cells in vitro. The kit may be used for diagnostic or research purposes by including all or part of the components necessary to perform a disclosed method. As a non-limiting example, an in vitro diagnostic (IVD) kit may contain one or more reagents for the detection or determination of gene expression as disclosed herein. The determination may be as part of an identification, classification, or subtyping as described.

The disclosure may be applied to identify the subtype of neuroendocrine cancer in a patient in a wide variety of cases including, but not limited to, identification of the subtype in a clinical setting. In some embodiments, the identification is made by classification of a cell containing sample known to contain cancer cells, but the neuroendocrine nature, and/or neuroendocrine subtype, of those cells is unknown. In other embodiments, the identification is made by classification of a cell containing sample as containing one or more cancer cells followed by identification of the cancer cell(s) as neuroendocrine tumor cells. In further embodiments, the disclosure is practiced with a sample from a subject with a previous history of cancer, and identification is made by classification of a cell as either being neuroendocrine cancer from a previous origin or of a new origin. Additional embodiments include those where multiple cancers are present in the same organ or tissue, and the disclosure is used to determine one or more of the cancers as a neuroendocrine tumor, as well as whether the cancers are of the same neuroendocrine subtype.

The disclosure is based upon the expression levels of the gene sequences in a set of known neuroendocrine tumor cells. These gene expression profiles (of gene sequences in the different known tumor cells or subtypes thereof), whether embodied in nucleic acid expression, protein expression, or other expression formats, may be compared to the expression levels of the same sequences in an unknown tumor sample to identify the sample as containing a neuroendocrine tumor and/or of a particular known subtype thereof. The disclosure provides, such as in a clinical setting, the advantages of a more accurate identification of a neuroendocrine tumor and thus the treatment thereof as well as the prognosis, including survival and/or likelihood of cancer recurrence following treatment, of the subject from whom the sample was obtained.

In some embodiments, the disclosure provides a method that also comprises distinguishing metastatic pancreatic endocrine tumors from other well-differentiated neuroendocrine carcinomas. The method may further comprise identifying, selecting, and/or providing a recognized therapy, such as tyrosine kinase and mTOR inhibitors as non-limiting examples, specifically recognized for pancreatic tumors.

The disclosure is also based in part on the discovery that use of expressed sequences as described herein as capable of identifying neuroendocrine tumors and/or classifying among subtypes thereof necessarily and effectively eliminates one or more known tumor types, or subtypes, from consideration during classification. This is in contrast to other approaches based upon the selection and use of highly correlated genes, which likely do not "rule out" other tumor types as opposed to "rule in" a tumor type based on a positive correlation between gene expression in a sample in comparison to a known reference tumor specimen.

This disclosure provides a non-subjective means for the identification of neuroendocrine tumors and/or subtype thereof in an afflicted subject. Where subjective interpretation may have been previously used to determine tissue source and/or cancer type, as well as the prognosis and/or treatment of the cancer based on that determination, the present disclosure provides objective gene expression patterns, which may used alone or in combination with subjective criteria to provide a more accurate identification of cancer classification. In some embodiments, the disclosed methods may be used in combination with protein-based detection of one or more of the polypeptides expressed by the disclosed genes. A non-limiting example of protein-based detection is immunohistochemical analysis for one or more of the polypeptides.

Additionally, this disclosure is particularly advantageously applied to samples of secondary or metastasized tumors, but any cell containing sample (including a primary tumor sample) for which the tissue source and/or tumor type is preferably determined by objective criteria may also be used with the disclosure. Of course the ultimate determination of class may be made based upon a combination of objective and non-objective (or subjective/partially subjective) criteria.

The disclosure includes its use as part of the clinical or medical care of a patient. Thus in addition to using an expression profile of genes as described herein to assay a cell containing sample from a subject afflicted with cancer to detect a neuroendocrine tumor and/or subtype thereof, the profile may also be used as part of a method to determine the prognosis of the cancer in the subject. The classification of the neuroendocrine tumor/cancer and/or the prognosis may be used to select or determine or alter the therapeutic treatment for said subject. Thus the classification methods of the disclosure may be directed toward the treatment of a neuroendocrine tumor, which is diagnosed in whole or in part based upon the classification. Given the diagnosis, administration of an appropriate anti-tumor agent or therapy, or the withholding or alternation of an anti-tumor agent or therapy may be used to treat the cancer.

The details of one or more embodiments of the disclosure are set forth in the accompanying drawing and the description below. Other features and advantages of the disclosure will be apparent from the drawings and detailed description, and from the claims.

DEFINITIONS

Figure 1:
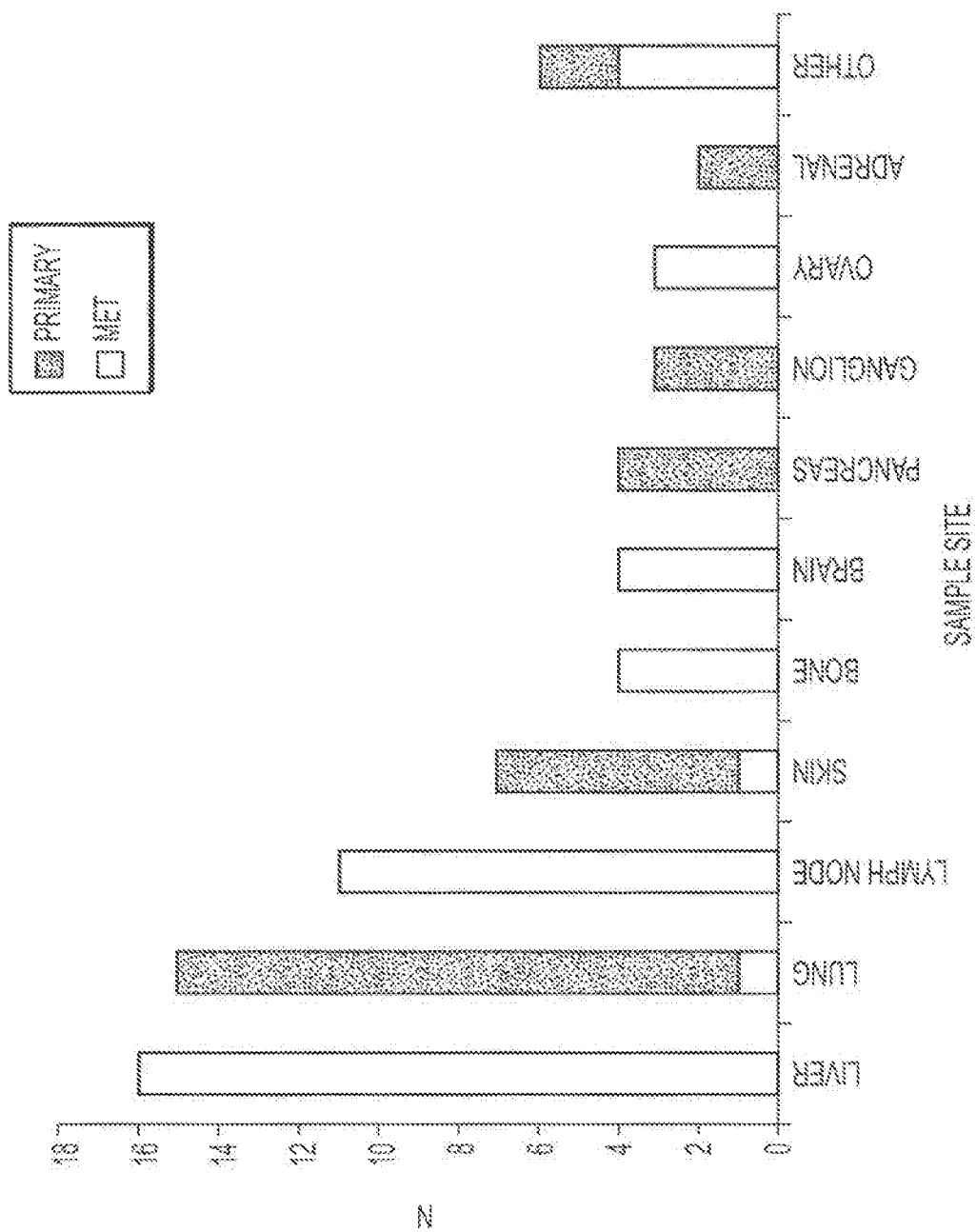
FIG. 1 illustrates the distribution of biopsy sites used in the Examples. The height of the bars represents the number of cases included from each biopsy site. Red bars indicate metastatic tumors to the sample site and blue bars indicate primary tumors at the sample site. The most common sites were liver metastases and lung primaries followed by lymph node metastases.

As used herein, a "gene" is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

A "sequence" or "gene sequence" as used herein is a nucleic acid molecule or polynucleotide composed of a discrete order of nucleotide bases. The term includes the ordering of bases that encodes a discrete product (i.e. "coding region"), whether RNA or proteinaceous in nature. It is appreciated that more than one polynucleotide may be capable of encoding a discrete product. It is also appreciated that alleles and polymorphisms of the human gene sequences may exist and may be used in the practice of the disclosure to identify the expression level(s) of the gene sequences or an allele or polymorphism thereof. Identification of an allele or polymorphism depends in part upon chromosomal location and ability to recombine during mitosis.

An "expressed sequence" is a sequence that is transcribed by cellular processes within a cell. To detect an expressed sequence, a region of the sequence that is unique relative to other expressed sequences may be used. An expressed sequence may encode a polypeptide product or not be known to encode any product. So an expressed sequence may contain open reading frames or no open reading frames. Non-limiting examples include regions of about 8 or more, about 10 or more, about 12 or more, about 14 or more, about 16 or more, about 18 or more, about 20 or more, about 22 or more, about 24 or more, about 26 or more, about 28 or more, or about 30 or more contiguous nucleotides within an expressed sequence may be used. The term "about" as used in the previous sentence refers to an increase or decrease of 1 from the stated numerical value. The physical form of an expressed sequence may be an RNA molecule or the corresponding cDNA molecule. Both an RNA molecule and a corresponding cDNA molecule (or strand) may be labeled to aid its detection in the practice of this disclosure.

The terms "correlate" or "correlation" or equivalents thereof refer to an association between expression of one or more genes and another event, such as, but not limited to, physiological phenotype or characteristic, such as neuroendocrine tumor type.

A "polynucleotide" is a polymeric form of nucleotides of any length, either ribonucleotides or deoxyribonucleotides, that embodies a sequence. This term refers to the primary structure of a molecule, such as that of an expressed sequence. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide. A polynucleotide of the disclosure, such as an expressed RNA, may be optionally labeled to aid in its detection.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence. Methods for amplifying mRNA are generally known in the art, and include reverse transcription PCR (RT-PCR) and quantitative PCR (or Q-PCR) or real time PCR. Alternatively, RNA may be directly labeled for detection or indirectly labeled as the corresponding cDNA by methods known in the art.

By "corresponding", it is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al. (1990), J. Mol. Biol. 215:403-410 (using the published default setting, i.e. parameters w=4, t=17).

A "microarray" is a linear or two-dimensional or three dimensional (and solid phase) array of discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, such as of at least about 50/cm$^2$, at least about 100/cm$^2$, or at least about 500/cm$^2$, up to about 1,000/cm$^2$ or higher. The arrays may contain less than about 500, about 1000, about 1500, about 2000, about 2500, or about 3000 immobilized polynucleotides in total. As used herein, a DNA microarray is an array of oligonucleotide or polynucleotide probes placed on a chip or other surfaces used to hybridize to amplified or cloned polynucleotides from a sample. Since the position of each particular group of probes in the array is known, the identities of a sample polynucleotides can be determined based on their binding to a particular position in the microarray. As an alternative to the use of a microarray, an array of any size may be used in the practice of the disclosure, including an arrangement of one or more position of a two-dimensional or three dimensional arrangement in a solid phase to detect expression of a single gene sequence. In some embodiments, a microarray for use with the present disclosure may be prepared by photolithographic techniques (such as synthesis of nucleic acid probes on the surface from the 3' end) or by nucleic synthesis followed by deposition on a solid surface.

Where the disclosure relies upon the identification of gene expression, some embodiments of the disclosure determine expression by hybridization of expressed RNA, such as mRNA, or an amplified or cloned version thereof, of a sample cell to a polynucleotide that is unique to a particular gene sequence. Polynucleotides of this type contain at least about 16, at least about 18, at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Other embodiments are polynucleotides of at least or about 50, at least or about 100, at least about or 150, at least or about 200, at least or about 250, at least or about 300, at least or about 350, at least or about 400, at least or about 450, or at least or about 500 consecutive bases of a sequence that is not found in other gene sequences. The term "about" as used in the preceding sentence refers to an increase or decrease of 10% from the stated numerical value. Longer polynucleotides may of course contain minor mismatches (e.g. via the presence of mutations) which do not affect hybridization to the nucleic acids of a sample. Such polynucleotides may also be referred to as polynucleotide probes that are capable of hybridizing to sequences of the genes, or unique portions thereof, described herein. Such polynucleotides may be labeled to assist in their detection. The sequences may be those of expressed RNA, such as mRNA, encoded by the genes, the corresponding cDNA to such RNAs, and/or amplified versions of such sequences. In some embodiments of the disclosure, the polynucleotide probes are immobilized on an array, other solid support devices, or in individual spots that localize the probes.

In other embodiments of the disclosure, all or part of a gene sequence may be amplified and detected by methods such as the polymerase chain reaction (PCR) and variations thereof, such as, but not limited to, quantitative PCR (Q-PCR), reverse transcription PCR (RT-PCR), and real-time PCR (including as a means of measuring the initial amounts of mRNA copies for each sequence in a sample), optionally real-time RT-PCR or real-time Q-PCR. Such methods would utilize one or two primers that are complementary to portions of a gene sequence, where the primers are used to prime nucleic acid synthesis. The newly synthesized nucleic acids are optionally labeled and may be detected directly or by hybridization to a polynucleotide of the disclosure. The newly synthesized nucleic acids may be contacted with polynucleotides (containing sequences) of the disclosure under conditions which allow for their hybridization. Additional methods to detect the expression of expressed nucleic acids include RNAse protection assays, including liquid phase hybridizations, and in situ hybridization of cells.

In additional embodiments, an expressed sequence may be detected by sequencing methods known to the skilled person. In some cases, an expressed RNA is first converted to one or both corresponding cDNA strands. The cDNA is then sequenced, optionally after its immobilization, to detect the presence of the expressed sequence. A cDNA may be sequenced by any method known to the skilled person, such as by annealing a primer that is complementary in whole or in part to the cDNA followed by primer extension (or polymerization) and detection of the extension product(s). In other cases, the cDNA may be ligated to a known sequence (such as a double-stranded DNA linker or adapter as non-limiting examples), at one or both ends of the cDNA. The result may then be sequenced by annealing a primer that is complementary to at least a portion of the known sequence followed by primer extension (or polymerization) and detection of the extension product(s).

Alternatively, and in further embodiments of the disclosure, gene expression may be determined by analysis of expressed protein in a cell sample of interest by use of one or more antibodies specific for one or more epitopes of individual gene products (proteins), or proteolytic fragments thereof, in said cell sample or in a bodily fluid of a subject. The cell sample may be one of breast cancer epithelial cells enriched from the blood of a subject, such as by use of labeled antibodies against cell surface markers followed by fluorescence activated cell sorting (FACS). Such antibodies may be labeled to permit their detection after binding to the gene product. Detection methodologies suitable for use in the practice of the disclosure include, but are not limited to, immunohistochemistry of cell containing samples or tissue, enzyme linked immunosorbent assays (ELISAs) including antibody sandwich assays of cell containing tissues or blood samples, mass spectroscopy, and immuno-PCR.

The terms "label" or "labeled" refer to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

"Expression" and "gene expression" include transcription and/or translation of nucleic acid material. Expression levels of an expressed sequence may optionally be normalized by reference or comparison to the expression level(s) of one or more control expressed genes. These "normalization genes" have expression levels that are relatively constant in all members of the plurality or group of known tumor types.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present disclosure is based on the relative level of gene expression, mutations in non-coding regions of genes as disclosed herein may also be assayed in the practice of the disclosure.

"Detection" or "detecting" includes any means of detecting, including direct and indirect determination of the level of gene expression and changes therein.

Unless defined otherwise all technical and scientific terms used herein have the same meaning as commonly understood to one of ordinary skill in the art to which this disclosure belongs.

DETAILED DESCRIPTION OF MODES OF PRACTICING THE DISCLOSURE

This disclosure provides methods for the use of gene expression information to identify and/or classify neuroendocrine tumors in a more objective manner than possible with conventional pathology techniques. The disclosure is based in part on the identification of expressed sequences that facilitate the identification of a neuroendocrine tumor by exclusion of other possible tumor types. The representative, and non-limiting, mRNA sequences corresponding to a set of four (4) gene sequences for use in the practice of this aspect of the disclosure are disclosed below. These four gene sequences have been previously disclosed in U.S. Patent Publications US 2006/0094035 and US 2007/0020655. The listing of identifying information, including accession numbers, Gene Symbols, and Description, of the four is in Table 1.

TABLE 1

| Accession number | Gene Symbol | Description |
|---|---|---|
| AY033998 | ELAVL4 | Onco-neural RNA binding protein, post-transcriptional gene expression, implicated in neuroendocrine cancer |
| BC015754 | CADPS | Neuroendocrine specific factor required for Ca++ regulated exocytosis of secretory vesicles |
| BC013117 | RGS17 | GTPase activating protein; overexpressed in cancer, oncogenic |
| AI309080 | KCNJ11 | Potassium inwardly rectifying channel, subfamily J, member 11 |

Thus in a first aspect, the disclosure provides a method of classifying a cell containing sample as containing neuroendocrine tumor cells. The method may comprise detecting, determining or measuring the expression levels of any one or two or more of the four sequences selected from AY033998 (ELAVL4), BC015754 (CADPS), BC013117 (RGS17) and AI309080 (KCNJ11) in cells of a cell containing sample obtained from a subject. In some embodiments of the method, one of the two or more sequences is AI309080 (KCNJ11). In other embodiments, the two or more sequences include BC013117 (RGS17) and AI309080 (KCNJ11). Of course any three of the four sequences may also be used in the practice of the method. Additional embodiments include use of all four sequences.

The cells of a cell containing sample may be cancer cells as would be recognized by the skilled pathologist or other skilled person based on observation and/or methodologies known in the field. The expression level may then be compared to the expression levels of the same one, two or more sequences in reference specimen(s) of known neuroendocrine tumor(s). A positive correlation, or optionally a match, between the expression levels in the sample and the reference specimen(s) may be used to classify or identify the sample as containing neuroendocrine tumor cells.

In some embodiments, the expression levels of expressed RNAs may be detected after labeling them by methods known to the skilled person. In other embodiments, the expression levels may be detected by analysis of cDNA copies of the expressed RNAs, optionally after amplification of the cDNA copies. In some embodiments, the expressed RNAs are mRNA molecules.

In additional aspects, the disclosure is based in part on the identification of expressed sequences that facilitate the identification of neuroendocrine tumor subtypes by exclusion of other possible tumor types. The representative, and non-limiting, mRNA sequences corresponding to a set of 15 gene sequences for use in the practice of this aspect of the disclosure are disclosed below. These 15 gene sequences have been previously disclosed in U.S. Patent Publications US 2006/0094035 and US 2007/0020655. The listing of identifying information, including Gene Symbols, alternate names, chromosomal location, and Description, of the 15 is in Table 2.

TABLE 2

| Gene Symbol | Alternate names | Location | Gene Function |
|---|---|---|---|
| KIF2C | Kinesin family member 2C, mitotic centromere associated kinesin (MCAK) | 1p34.1 | Encodes a kinesin-family protein; microtubule associated molecular motor that facilitates transport of organelles during anaphase; may be involved in coordinating sister chromatid separation.[31, 32] |

TABLE 2-continued

| Gene Symbol | Alternate names | Location | Gene Function |
|---|---|---|---|
| SFTA3 | Putative protein SFTA3, surfactant associated protein H | 14q13.3 | Putative protein; unknown. |
| CDCA3 | Cell division cycle associated protein 3, trigger of mitotic entry protein (Tome-1), gene rich cluster protein C8 | 12p13 | F-box like protein which is required for entry into mitosis. Acts by participating in E3 ligase complexes that mediate the ubiquitination and degradation of WEE1 kinase at the G2/M phase. May be targeted for degradation by APC.[33] |
| KIF12 | Kinesin family member 12, RP11-56P10.3 | 9q32 | Encodes a kinesin-family protein; microtubule associated molecular motor that uses ATP hydrolysis to facilitate transport of organelles during cell division.[31, 34] |
| CDH17 | Cadherin 17, cadherin 16, liver-intestine cadherin, human peptide transporter-1 (HPT-1) | 8q22.1 | Encodes a cadherin protein, a family of calcium dependent membrane-associated glycoproteins. In the gastrointestinal tract and pancreatic ducts, acts as a proton-dependent peptide transporter, the first step in oral absorption of many medically important drugs. May play a role in liver and intestine development. May be upregulated and be a poor prognostic factor in gastrointestinal, pancreatic, and hepatocellular cancers.[35-39] |
| LOC100130899 | Uncharacterized | 22q13.1 | Uncharacterized mRNA, no known coding protein |
| NBLA00301 | Differentially expressed in neuroblastoma (DEIN) | 4q34.1 | Unknown if coding or non-coding RNA. Novel gene has high expression levels in stage 4S neuroblastoma (disseminated neuroblastoma of infancy that spontaneously regresses).[40, 41] |
| HOXD11 | Homeobox D11, HOX4, HOX4F | 2q31.1 | Homeobox family gene, encodes protein important for limb and genitourinary development. May be involved in regulation of proliferation in cells with primitive neuronal differentiation. Aberrantly methylated in some ovarian cancers. Gene is part of a family of recurrent fusion transcripts in acute myeloid leukemia.[42-46] |
| EPS8L3 | Epidermal growth factor receptor pathway substrate 8-like protein 3, EPS8R3 | 1p13.3 | Related to EPS8, which is a substrate for EGFR; function unknown. |
| IRX3 | Iroquois-class homeodomain protein 3, IRX-1, IRXB1 | 16q12.2 | Iroquois homeobox gene family; role in early neural development. May play a role in obesity and type 2 diabetes.[47, 48] |
| WWC1 | WW and C2 domain containing protein 1, kidney and brain protein (KIBRA), HBeAg binding protein 3 (HBEBP3), HBEBP36 | 5q34 | Cytoplasmic phosphoprotein; interacts with PRKC-zeta and dynein light chain 1. Polymorphisms are associated with enhanced memnory capabilities. Methylation common in B-cell acute lymphoblastic leukemia; methylation a poor prognostic factor in chronic lymphocytic leukemia.[49-53] |
| HOXB8 | Homeobox B8, HOX2, HOX2D, Hox-2.4 | 17q21.3 | Transcription factor important for anterior-posterior axis development. Involved in myeloid differentiation. Upregulated in colorectal cancer. May be associated with obsessive-compulsive behavior.[54-56] |
| FOXG1 | Forkhead box protein G1, oncogene QIN, brain factor 1 (BF1), BF2, HBF2, forkhead-like 1, FKH2; HFK1; HFK2; HFK3; KHL2; FHKL3; FKHL 1; FKHL2; FKHL3; FKHL4; HBF-1; HBF-2; HBF-3; FOXG1A; FOXG1B; FOXG1C; HBF-G2 | 14q13 | Encodes forkhead transcription factor family protein; may play a role in brain development; mutations and duplications associated with a spectrum of neurodevelopmental syndromes. Overexpressed in primitive embryonic tumors (medulloblastoma, hepatoblastoma).[57-62] |

TABLE 2-continued

| Gene Symbol | Alternate names | Location | Gene Function |
|---|---|---|---|
| BCL11B | B-cell CLL/lymphoma 11B, radiation induced tumor suppressor gene 1 protein (RIT1), hRIT alpha, COUP-TF-interacting protein 2 (CTIP2), ZNF856B | 14q32.2 | C2H2-type zinc finger protein; may be associated with B-cell malignancies. May play a key role in thymocyte development. May be involved as a tumor suppressor in the p53 pathway. Mutated in many T-cell acute lymphoblastic leukemias.[63-65] |
| LOC100506088 | Uncharacterized | 2p21 | cDNA discovered in a pulmonary carcinoid tumor; function unknown. |

Accession numbers corresponding to the 15 genes in Table 2 are shown below in Table 3.

TABLE 3

| Accession number | Gene Symbol |
|---|---|
| BC008764 | KIF2C |
| AK027147 | SFTA3 |
| BC002551 | CDCA3 |
| BC010626 | KIF12 |
| NM_004063 | CDH17 |
| BE552004 | LOC100130899 |
| AK054605 | DEIN |
| AW194680 | HOXD11 |
| BC012926 | EPS8L3 |
| AI804745 | IRX3 |
| AI685931 | WWC1 |
| BF437393 | HOXB8 |
| AL039118 | FOXG1 |
| H09748 | BCL11B |
| BF224381 | LOC100506088 |

Thus the disclosure provides an additional method of classifying a cell containing sample as containing a subtype of neuroendocrine tumor cells. The method may comprise detecting, determining or measuring the expression levels of any two (2) or more sequences selected from the 15 sequences described above in cells of a cell containing sample obtained from a subject. Of course any three or more, four or more, five or more, six or more, seven or more, eight or more, nine or more, 10 or more, 11 or more, 12 or more, 13 or more, 14 or all 15 of the sequences may be used in the practice of the method. Additional embodiments include use of all four sequences.

The cells of a cell containing sample may be cancer cells as would be recognized by the skilled pathologist or other skilled person based on observation and/or methodologies known in the field. In some cases, the cancer cells may be neuroendocrine tumor or NEC cells identified by a disclosed method. The expression level may be compared to the expression levels of the same two or more sequences in a plurality of reference specimen(s) of known neuroendocrine tumor subtypes. A positive correlation, or optionally a match, between the expression levels in the sample and a reference subtype specimen within the plurality may be used to classify or identify the sample as containing neuroendocrine tumor cells of that subtype. As used herein, "a plurality" refers to the state of two or more.

In some cases, the plurality includes one or more known neuroendocrine tumor specimens of adrenal-pheochromocytoma/paraganglioma, gastrointestinal neuroendocrine tumor, pulmonary carcinoid, pulmonary small cell or large cell carcinoma, pancreatic neuroendocrine tumor, Merkel cell carcinoma, and medullary thyroid carcinoma.

In some embodiments, the expression levels of expressed RNAs may be detected after labeling them by methods known to the skilled person. In other embodiments, the expression levels may be detected by analysis of cDNA copies of the expressed RNAs, optionally after amplification of the cDNA copies. In some embodiments, the expressed RNAs are mRNA molecules.

As described herein, the disclosed methods of identifying and classifying are based upon a comparison of the expression levels of the assayed transcribed sequences in the cells of a sample to their expression levels in known neuroendocrine tumor specimens and/or known subtypes thereof. So as a non-limiting example, the expression levels of the gene sequences may be determined in a set of known neuroendocrine tumor samples, and/or known subtypes thereof, to provide a database against which the expression levels detected or determined in a cell containing sample from a subject is compared. As described below and in embodiments of the disclosure utilizing Q-PCR or real time Q-PCR, the expression levels may be compared to expression levels of reference genes in the same sample or a ratio of expression levels may be used.

While the disclosure is described mainly with respect to human subjects, samples from other subjects may also be used. Performance with other subjects is possible with the ability to assess the expression levels of gene sequences in a plurality of known neuroendocrine tumor specimens such that the expression levels in an unknown or test sample may be compared. Thus the disclosure may be applied to samples from another organism for which a plurality of expressed sequences, and a plurality of known tumor samples, are available. One non-limiting example is application of the disclosure to mouse samples, based upon the availability of the mouse genome to permit detection of expressed murine sequences and the availability of known mouse tumor samples or the ability to obtain known samples. Thus, the disclosure is contemplated for use with other samples, including those of mammals, primates, and animals used in clinical testing (such as rats, mice, rabbits, dogs, cats, and chimpanzees) as non-limiting examples.

While the disclosure is readily practiced with the use of cell containing samples, practice of the disclosure is possible with other nucleic acid containing samples which may be assayed for gene expression levels. Without limiting the disclosure, a sample as described herein may be one that is suspected or known to contain tumor cells. Alternatively, a sample of the disclosure may be a "tumor sample" or "tumor containing sample" or "tumor cell containing sample" of tissue or fluid isolated from an individual suspected of being afflicted with, or at risk of developing, cancer. Non-limiting examples of samples for use with the disclosure include a clinical sample, such as, but not limited to, a fixed sample, a fresh sample, or a frozen sample. The sample may be an aspirate, a cytological sample (including blood or other bodily fluid, including fluid from an ascites or a pleural cavity), a sample from a lymph node, or a tissue specimen, which includes at least some information regarding the in situ context of cells in the specimen, so long as appropriate cells or nucleic acids are available for determination of gene expression levels.

Non-limiting examples of fixed samples include those that are fixed with formalin or formaldehyde (including FFPE samples), with Boudin's, glutaldehyde, acetone, alcohols, or any other fixative, such as those used to fix cell or tissue samples for immunohistochemistry (IHC). Other examples include fixatives that precipitate cell associated nucleic acids and proteins. Given possible complications in handling frozen tissue specimens, such as the need to maintain its frozen state, the disclosure may be practiced with non-frozen samples, such as fixed samples, fresh samples, including cells from blood or other bodily fluid or tissue, and minimally treated samples. In some applications of the disclosure, the sample has not been classified using standard pathology techniques, such as, but not limited to, immunohistochemistry based assays.

In other embodiments, the gene expression levels of other gene sequences may be determined along with the above described determinations of expression levels for use in classification. One non-limiting example of this is seen in the case of a microarray based platform to determine gene expression, where the expression of other gene sequences is also measured. Where those other expression levels are not used in comparison to expression in known tumor types, they may be considered the results of "excess" transcribed sequences and not critical to the practice of the disclosure. Alternatively, and where those other expression levels are used in classification, they are within the scope of the disclosure, where the description of using particular numbers of sequences does not necessarily exclude the use of expression levels of additional sequences. In some embodiments, the disclosure includes the use of expression level(s) from one or more "excess" gene sequences, such as those which may provide information redundant to one or more other gene sequences used in a method of the disclosure.

The practice of the disclosure to classify a cell containing sample as having a neuroendocrine tumor cell may be by use of an appropriate classification algorithm that utilizes supervised learning to accept 1) the levels of expression of the gene sequences in a plurality of known neuroendocrine tumors or subtypes thereof as a training set and 2) the levels of expression of the same genes in one or more cells of a sample to classify the sample as having cells of a neuroendocrine tumor or subtypes thereof. Such algorithms are known to the skilled person. The levels of expression may be provided based upon the signals in any format, including nucleic acid expression or protein expression as described herein.

Embodiments of the disclosure include use of the methods and materials described herein to identify the cancer from a patient as may be found in a lymph node. Thus given a sample containing tumor cells from a lymph node, such as the case of a subject with an inflamed lymph node containing cancer cells, may be used. The present disclosure may be used to classify the cells as being of a neuroendocrine tumor, and/or a subtype thereof.

In further embodiments, the disclosure is practiced with a sample from a subject with a previous history of cancer. As a non-limiting example, a cell containing sample (from the lymph node or elsewhere) of the subject may be found to contain cancer cells such that the present disclosure may be used to determine whether the cells are from the same or a different tissue from that of the previous cancer. The disclosure may be used to identify the new cancer cells as being the result of metastasis from the previous cancer (or from another tumor type, whether previously identified or not).

mRNA sequences corresponding to 15 of the 19 disclosed gene sequences are provided as follows:

Hs.75236_mRNA_4 gi|14280328|gb|AY033998.1| *Homo sapiens* polyA=3

Hs.285508_contig1 AW194680|BF939744|BF516467 poly A=1 polyA=1

Hs.183274_contig1 BF437393|BF064008|BF509951| W134603|AI277015|AI803254|AA887915|BF054958|AI-004413|AI393911|AI278517|AW612664|AI492162|AI30-9226|AI863671|AA448864|AI640165|AA479926|AA461-188|AA780161|BF591180|AI918020|AI758226|AI29137-5|BF001845|BF003064|AI337393|AI522206|BE856784| BF001760|AI280300 FLAG=1 polyA=2 WARN polyA=3

Hs.3321_contig1 AI804745|AI492375|AA594799|BE672611|AA814147| AA722404|AW170088|D11718|BG15-3444|AI680648| AA063561|BE219054|AI590287|R55185|AI479167| AI796872|AI018324|AI70-1122|BE218203|AA905336| AI681917|BI084742|AI480008|AI217994|AI401468 polyA=2 polyA=3

Hs.351486_mRNA_1 gi|16549178|dbj|AK054605.1|AK054605 *Homo sapiens* cDNA FLJ30043 fis, clone 3NB692001548 polyA=0

Hs.69360_mRNA_2 gi|14250609|gb|BC008764.1|BC008764 *Homo sapiens* clone MGC: 1266 IMAGE: 3347571 polyA=3

Hs.5366_mRNA_2 gi|15277845|gb|BC012926.1|BC012926 *Homo sapiens* clone MGC: 16817 IMAGE: 3853503 polyA=3

Hs.18140_contig1 AI685931|AA410954|T97707|AA706873|AI911572| AW614616|AA548520|AW027764|BF51-1251|AI914294| AW151688 polyA=1 polyA=1

Hs.133196_contig2 BF224381|BE467992|AW137689|AI695045|AW207361| BF445141|AA405473 polyA=2 WARN polyA=3

Hs.94367_mRNA_1 gi|10440200|dbj|AK027147.1|AK027147 *Homo sapiens* cDNA: FLJ23494 fis, clone LNG01885 polyA=3

Hs.155977_contig1 AI309080|AI313045 polyA=1 WARN polyA=1

Hs.28149_mRNA_1 gi|14714936|gb|BC010626.1|BC010626 *Homo sapiens* clone MGC: 17687 IMAGE: 3865868 polyA=3

Hs.268562_mRNA_2 gi|15341874|gb|BC013117.1|BC013117 *Homo sapiens* clone MGC: 8711 IMAGE: 3882749 polyA=3

Hs.151301_mRNA_3 gi|16041747|gb|BC015754.1|BC015754 *Homo sapiens* clone MGC: 23085 IMAGE: 4862492 polyA=3

Hs.89436_mRNA_1 gi|16507959|ref|NM_004063.2| *Homo sapiens* cadherin 17, LI cadherin (liver-intestine) (CDH17), mRNA polyA=1

As would be understood by the skilled person, detection of expression of any of the disclosed sequences may be performed by the detection of expression of any appropriate portion or fragment of these sequences. Preferably, the portions are sufficiently large to contain unique sequences relative to other sequences expressed in a cell containing sample. Moreover, the skilled person would recognize that the disclosed sequences represent one strand of a double stranded molecule and that either strand may be detected as an indicator of expression of the disclosed sequences. This is because the disclosed sequences are expressed as RNA molecules in cells which may be converted to cDNA molecules for ease of manipulation and detection. The resultant cDNA molecules may have the sequences of the expressed RNA as well as those of the complementary strand thereto. Thus either the RNA sequence strand or the complementary strand may be detected. Of course is it also possible to detect the expressed RNA without conversion to cDNA.

In some embodiments of the disclosure, the expression levels of the above identified 15 of 19 gene sequences is measured by detection of expressed sequences in a cell containing sample as hybridizing to the following oligonucleotides, which correspond to the above sequences as indicated by the accession numbers provided.

BF437393
(SEQ ID NO: 1)
GGAGGGAGGGCTAATTATATATTTTGTTGTTCCTCTATACTTTGTTCTGT
TGTCTGCGCC

BF224381
(SEQ ID NO: 2)
TTCTCTTTTGGGGGCAAACACTATGTCCTTTTCTTTTTCTAGATACAGTT
AATTCCTGGA

AY033998
(SEQ ID NO: 3)
AGTGTTGCAAGTTTCCTTTAAAACCAACAAAGCCCACAAGTCCTGAATTT
CCCATTCTTA

BC015754
(SEQ ID NO: 4)
TCTGTAACTGCACAACCCTGGGGTTTGCTGCAGAGCTATTTCTTTCCATG
TAAAGTAGTG

AK027147
(SEQ ID NO: 5)
TTGTAATCATGCCAATTCCAGATCAATAACTGCATGTCTGTTCTTTGGTA
GAAATAGCTT

AK054605
(SEQ ID NO: 6)
TTCATTTCCAAACATCATCTTTAAGACTCCAAGGATTTTTCCAGGCACAG
TGGCTCATAC

AI804745
(SEQ ID NO: 7)
GGGTGGAGTTTCAGTGAGAATAAACGTGTCTGCCTTTGTGTGTGTATA
TATACAGAGA

BC008764
(SEQ ID NO: 8)
CTTTGGGCCGAGCACTGAATGTCTTGTACTTTAAAAAAATGTTTCTGAGA
CCTCTTTCTA

AI309080
(SEQ ID NO: 9)
CTGGACCCTTGGAGCAGTGTTGTGTGAACTTGCCTAGAACTCTGCCTTCT
CCGTTGTCAA

AW194680
(SEQ ID NO: 10)
TCCTTCCTCTTCGGTGAATGCAGGTTATTTAAACTTTGGGAAATGTACTT
TTAGTCTGTC

BC010626
(SEQ ID NO: 11)
CTCAGACTGGGCTCCACACTCTTGGGCTTCAGTCTGCCCATCTGCTGAAT
GGAGACAGCA

BC013117
(SEQ ID NO: 12)
CCTAATGGGGATTCCTCTGGTTGTTCACTGCCAAAACTGTGGCATTTTCA
TTACAGGAGA

NM_004063
(SEQ ID NO: 13)
GCCATGCATACATGCTGCGCATGTTTTCTTCATTCGTATGTTAGTAAAGT
TTTGGTTATT

BC012926
(SEQ ID NO: 14)
CACCTATTTATTTTACCTCTTTCCCAAACCTGGAGCATTTATGCCTAGGC
TTGTCAAGAA

AI685931
(SEQ ID NO: 15)
AATTCTCTATAAACGGTTCACCAGCAAACCACCAATACATTCCATTGTTT
GCCTAGAGAG

Expression levels of the remaining 4 of 19 gene sequences may be measured by detection of expressed sequences in a cell containing sample as hybridizing to the following oligonucleotides, which are identified by the accession numbers provided.

H09748
(SEQ ID NO: 16)
TGAGTTCAGCATGTGTCTGTCCATTTCATTTGTACGCTTGTTCAAAACCA
AGTTTGTTCT

BC002551
(SEQ ID NO: 17)
TACCAAACTGGGACTCACAGCTTTATTGGGCTTTCTTTGTGTCTTGTGTG
TTTCTTTTAT

AL039118
(SEQ ID NO: 18)
TTGTCTTAAAATTTCTTGATTGTGATACTGTGGTCATATGCCCGTGTTTG
TCACTTACAA

BE552004
(SEQ ID NO: 19)
TTGTGCAAAAGTCCCACAACCTTTCTGGATTGATAGTTTGTGGTGAAATA
AACAATTTTA

As used herein, a "tumor sample" or "tumor containing sample" or "tumor cell containing sample" or variations thereof, refer to cell containing samples of tissue or fluid isolated from an individual suspected of being afflicted with, or at risk of developing, cancer. The samples may contain tumor cells which may be isolated by known methods or other appropriate methods as deemed desirable by the skilled practitioner. These include, but are not limited to, microdissection, laser capture microdissection (LCM), or laser microdissection (LMD) before use in the instant disclosure. Alternatively, undissected cells within a "section" of tissue may be used. Non-limiting examples of such samples include primary isolates (in contrast to cultured cells) and may be collected by any non-invasive or minimally invasive means, including, but not limited to, ductal lavage, fine needle aspiration, needle biopsy, the devices and methods described in U.S. Pat. No. 6,328,709, or any other suitable means recognized in the art. Alternatively, the sample may be collected by an invasive method, including, but not limited to, surgical biopsy.

The detection and measurement of transcribed sequences may be accomplished by a variety of means known in the art or as deemed appropriate by the skilled practitioner. Essentially, any assay method may be used as long as the assay reflects, quantitatively or qualitatively, the level of expression of the transcribed sequence being detected.

The ability to classify tumor samples is provided by the recognition of the relevance of the level of expression of the gene sequences (whether randomly selected or specific) and not by the form of the assay used to determine the actual level of expression. An assay of the disclosure may utilize any identifying feature of a individual gene sequence as disclosed herein as long as the assay reflects, quantitatively or qualitatively, expression of the gene in the "transcriptome" (the transcribed fraction of genes in a genome) or the "proteome" (the translated fraction of expressed genes in a genome). Additional assays include those based on the detection of polypeptide fragments of the relevant member or members of the proteome. Non-limiting examples of the latter include detection of proteolytic fragments found in a biological fluid, such as blood or serum. Identifying features include, but are not limited to, unique nucleic acid sequences used to encode (DNA), or express (RNA), said gene or epitopes specific to, or activities of, a protein encoded by a gene sequence.

In some embodiments, all or part of a gene sequence may be amplified and detected by methods such as the polymerase chain reaction (PCR) and variations thereof, such as, but not limited to, quantitative PCR (Q-PCR), reverse transcription PCR (RT-PCR), and real-time PCR (including as a means of measuring the initial amounts of mRNA copies for each sequence in a sample), optionally real-time RT-PCR or real-time Q-PCR. Such methods would utilize one or two primers that are complementary to portions of a gene sequence, where the primers are used to prime nucleic acid synthesis. The newly synthesized nucleic acids are optionally labeled and may be detected directly or by hybridization to a polynucleotide of the disclosure. The newly synthesized nucleic acids may be contacted with polynucleotides (containing gene sequences) of the disclosure under conditions which allow for their hybridization. Because the disclosure may be practiced with the use of expression levels of more than two of the disclosed expressed gene sequences, the disclosure includes use of multiplex PCR or microarrays to facilitate the measurement of gene expression. Additional methods to detect the expression of expressed nucleic acids include RNAse protection assays, including liquid phase hybridizations, and in situ hybridization of cells.

Alternatively, the expression of gene sequences in FFPE samples may be detected as disclosed in U.S. Pat. No. 7,364,846 B2 (which is hereby incorporated by reference as if fully set forth). Briefly, the expression of all or part of an expressed gene sequence or transcript may be detected by use of hybridization mediated detection (such as, but not limited to, microarray, bead, or particle based technology) or quantitative PCR mediated detection (such as, but not limited to, real time PCR and reverse transcriptase PCR) as non-limiting examples. The expression of all or part of an expressed polypeptide may be detected by use of immunohistochemistry techniques or other antibody mediated detection (such as, but not limited to, use of labeled antibodies that bind specifically to at least part of the polypeptide relative to other polypeptides) as non-limiting examples. Additional means for analysis of gene expression are available, including detection of expression within an assay for global, or near global, gene expression in a sample (e.g. as part of a gene expression profiling analysis such as on a microarray).

In embodiments using a nucleic acid based assay to determine expression includes immobilization of one or more gene sequences on a solid support, including, but not limited to, a solid substrate as an array or to beads or bead based technology as known in the art. Alternatively, solution based expression assays known in the art may also be used. The immobilized gene sequence(s) may be in the form of polynucleotides that are unique or otherwise specific to the gene(s) such that the polynucleotides would be capable of hybridizing to the DNA or RNA of said gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary basepairs) such that hybridization with a DNA or RNA corresponding to the genes is not affected. In some embodiments, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal. Thus the practice of the present disclosure is unaffected by the presence of minor mismatches between the disclosed sequences and those expressed by cells of a subject's sample. A non-limiting example of the existence of such mismatches are seen in cases of sequence polymorphisms between individuals of a species, such as individual human patients within *Homo sapiens*.

As known by those skilled in the art, some gene sequences include 3' poly A (or poly T on the complementary strand) stretches that do not contribute to the uniqueness of the disclosed sequences. The disclosure may thus be practiced with gene sequences lacking the 3' poly A (or poly T) stretches. The uniqueness of the disclosed sequences refers to the portions or entireties of the sequences which are found only in nucleic acids, including unique sequences found at the 3' untranslated portion thereof. Some unique sequences for the practice of the disclosure are those which contribute to the consensus sequences for the genes such that the unique sequences will be useful in detecting expression in a variety of individuals rather than being specific for a polymorphism present in some individuals. Alternatively, sequences unique to an individual or a subpopulation may be used. The unique sequences may be the lengths of polynucleotides of the disclosure as described herein.

In additional embodiments of the disclosure, polynucleotides having sequences present in the 3' untranslated and/or non-coding regions of gene sequences are used to detect expression levels in cell containing samples of the disclosure. Such polynucleotides may optionally contain sequences found in the 3' portions of the coding regions of gene sequences. Polynucleotides containing a combination of sequences from the coding and 3' non-coding regions preferably have the sequences arranged contiguously, with no intervening heterologous sequence(s).

Alternatively, the disclosure may be practiced with polynucleotides having sequences present in the 5' untranslated and/or non-coding regions of gene sequences to detect the level of expression in cells and samples of the disclosure. Such polynucleotides may optionally contain sequences found in the 5' portions of the coding regions. Polynucleotides containing a combination of sequences from the coding and 5' non-coding regions may have the sequences arranged contiguously, with no intervening heterologous sequence(s). The disclosure may also be practiced with sequences present in the coding regions of gene sequences.

The polynucleotides of some embodiments contain sequences from 3' or 5' untranslated and/or non-coding regions of at least about 16, at least about 18, at least about 20, at least about 22, at least about 24, at least about 26, at least about 28, at least about 30, at least about 32, at least about 34, at least about 36, at least about 38, at least about 40, at least about 42, at least about 44, or at least about 46 consecutive nucleotides. The term "about" as used in the previous sentence refers to an increase or decrease of 1 from the stated numerical value. Other embodiments use polynucleotides containing sequences of at least or about 50, at least or about 100, at least about or 150, at least or about 200, at least or about 250, at least or about 300, at least or about 350, or at least or about 400 consecutive nucleotides. The term "about" as used in the preceding sentence refers to an increase or decrease of 10% from the stated numerical value.

Sequences from the 3' or 5' end of gene coding regions as found in polynucleotides of the disclosure are of the same lengths as those described above, except that they would naturally be limited by the length of the coding region. The 3' end of a coding region may include sequences up to the 3' half of the coding region. Conversely, the 5' end of a coding region may include sequences up the 5' half of the coding region. Of course the above described sequences, or the coding regions and polynucleotides containing portions thereof, may be used in their entireties.

In another embodiment of the disclosure, polynucleotides containing deletions of nucleotides from the 5' and/or 3' end of gene sequences may be used. The deletions are preferably of 1-5, 5-10, 10-15, 15-20, 20-25, 25-30, 30-35, 35-40, 40-45, 45-50, 50-60, 60-70, 70-80, 80-90, 90-100, 100-125, 125-150, 150-175, or 175-200 nucleotides from the 5' and/or 3' end, although the extent of the deletions would naturally be limited by the length of the sequences and the need to be able to use the polynucleotides for the detection of expression levels.

Other polynucleotides of the disclosure from the 3' end of gene sequences include those of primers and optional probes for quantitative PCR. Preferably, the primers and probes are those which amplify a region less than about 750, less than about 700, less than about 650, less than about 6000, less than about 550, less than about 500, less than about 450, less than about 400, less than about 350, less than about 300, less than about 250, less than about 200, less than about 150, less than about 100, or less than about 50 nucleotides from the from the polyadenylation signal or polyadenylation site of a gene or expressed sequence. The size of a PCR amplicon of the disclosure may be of any size, including at least or about 50, at least or about 100, at least about or 150, at least or about 200, at least or about 250, at least or about 300, at least or about 350, or at least or about 400 consecutive nucleotides, all with inclusion of the portion complementary to the PCR primers used.

Other polynucleotides for use in the practice of the disclosure include those that have sufficient homology to gene sequences to detect their expression by use of hybridization techniques. Such polynucleotides preferably have about or 95%, about or 96%, about or 97%, about or 98%, or about or 99% identity with the gene sequences to be used. Identity is determined using the BLAST algorithm, as described above. The other polynucleotides for use in the practice of the disclosure may also be described on the basis of the ability to hybridize to polynucleotides of the disclosure under stringent conditions of about 30% v/v to about 50% formamide and from about 0.O1M to about 0.15M salt for hybridization and from about 0.O1M to about 0.15M salt for wash conditions at about 55 to about 65° C. or higher, or conditions equivalent thereto.

In a further embodiment of the disclosure, a population of single stranded nucleic acid molecules comprising one or both strands of a human gene sequence is provided as a probe such that at least a portion of said population may be hybridized to one or both strands of a nucleic acid molecule quantitatively amplified from RNA of a cell or sample of the disclosure. The population may be only the antisense strand of a human gene sequence such that a sense strand of a molecule from, or amplified from, a cell may be hybridized to a portion of said population. The population preferably comprises a sufficiently excess amount of said one or both strands of a human gene sequence in comparison to the amount of expressed (or amplified) nucleic acid molecules containing a complementary gene sequence.

In additional embodiments, the disclosure may be practiced by analyzing gene expression from single cells or homogenous cell populations which have been dissected away from, or otherwise isolated or purified from, contaminating cells of a sample as present in a simple biopsy. One advantage provided by these embodiments is that contaminating, non-tumor cells (such as infiltrating lymphocytes or other immune system cells) may be removed as so be absent from affecting the genes identified or the subsequent analysis of gene expression levels as provided herein. Such contamination is present where a biopsy is used to generate gene expression profiles.

In further embodiments of the disclosure utilizing Q-PCR or reverse transcriptase Q-PCR as the assay platform, the expression levels of gene sequences of the disclosure may be compared to expression levels of reference genes in the same sample or a ratio of expression levels may be used. This provides a means to "normalize" the expression data for comparison of data on a plurality of known tumor types and a cell containing sample to be assayed. Moreover, the Q-PCR may be performed in whole or in part with use of a multiplex format.

In an additional aspect, the methods provided by the present disclosure may also be automated in whole or in part. This includes the embodiment of the disclosure in software. Non-limiting examples include processor executable instructions on one or more computer readable storage devices wherein said instructions direct the classification of tumor samples based upon gene expression levels as described herein. Additional processor executable instructions on one or more computer readable storage devices are contemplated wherein said instructions cause representation and/or manipulation, via a computer output device, of the process or results of a classification method.

The disclosure includes software and hardware embodiments wherein the gene expression data of a set of gene sequences in a plurality of known tumor types is embodied as a data set. In some embodiments, the gene expression data set is used for the practice of a method of the disclosure. The disclosure also provides computer related means and systems for performing the methods disclosed herein. In some embodiments, an apparatus for classifying a cell containing sample is provided. Such an apparatus may comprise a query input configured to receive a query storage configured to store a gene expression data set, as described herein, received from a query input; and a module for accessing and using data from the storage in a classification algorithm as described herein. The apparatus may further comprise a string storage for the results of the classification algorithm, optionally with a module for accessing and using data from the string storage in an output algorithm as described herein.

The steps of a method, process, or algorithm described in connection with the embodiments disclosed herein may be embodied directly in hardware, in a software module executed by a processor, or in a combination of the two. The various steps or acts in a method or process may be performed in the order shown, or may be performed in another order. Additionally, one or more process or method steps may be omitted or one or more process or method steps may be added to the methods and processes. An additional step, block, or action may be added in the beginning, end, or intervening existing elements of the methods and processes.

A further aspect of the disclosure provides for the use of the present disclosure in relation to clinical activities. In some embodiments, the determination or measurement of gene expression as described herein is performed as part of providing medical care to a patient, including the providing of diagnostic services in support of providing medical care. Thus the disclosure includes a method in the medical care of a patient, the method comprising determining or measuring expression levels of gene sequences in a cell containing sample obtained from a patient as described herein. The method may further comprise the classifying of the sample, based on the determination/measurement, as including a neuroendocrine tumor cell or subtype thereof in a manner as described herein. The determination and/or classification may be for use in relation to any aspect or embodiment of the disclosure as described herein.

The determination or measurement of expression levels may be preceded by a variety of related actions. In some embodiments, the measurement is preceded by a determination or diagnosis of a human subject as in need of said measurement. The measurement may be preceded by a determination of a need for the measurement, such as that by a medical doctor, nurse or other health care provider or professional, or those working under their instruction, or personnel of a health insurance or maintenance organization in approving the performance of the measurement as a basis to request reimbursement or payment for the performance. In some embodiments, the classification may be followed by payment for performance of a disclosed method.

The measurement may also be preceded by preparatory acts necessary to the actual measuring. Non-limiting examples include the actual obtaining of a cell containing sample from a human subject; or receipt of a cell containing sample; or sectioning a cell containing sample; or isolating cells from a cell containing sample; or obtaining RNA from cells of a cell containing sample; or reverse transcribing RNA from cells of a cell containing sample. The sample may be any as described herein for the practice of the disclosure.

The disclosure further provides kits for the determination or measurement of gene expression levels in a cell containing sample as described herein. Non-limiting kits include those for in vitro use, such as an in vitro diagnostic kit. A kit will typically comprise one or more reagents to detect gene expression as described herein for the practice of the present disclosure. Non-limiting examples include polynucleotide probes or primers for the detection of expression levels, one or more enzymes used in the methods of the disclosure, and one or more tubes for use in the practice of the disclosure.

In some embodiments, a kit will be suitable for detection of gene expression by amplification of expressed sequences, with PCR-based amplification as a non-limiting example, or by sequencing of expressed sequences. Optionally, the detection method is quantitative.

In other embodiments, the kit will include an array, or solid media capable of being assembled into an array, for the detection of gene expression as described herein. In other embodiments, the kit may comprise one or more antibodies that are immunoreactive with one or more epitopes present on a polypeptide which is expressed by a disclosed gene sequence or indicates expression of a gene sequence In some embodiments, the antibody may be an antibody fragment.

A kit of the disclosure may also include instructional materials disclosing or describing the use of the kit or a primer or probe of the present disclosure in a method of the disclosure as provided herein. Additionally, a kit may include reference data, or collective expression data, of gene expression in known specimens of neuroendocrine tumors or NECs as described herein.

A kit may also include additional components to facilitate the particular application for which the kit is designed. Thus, for example, a kit may additionally contain means of detecting the label (e.g. enzyme substrates for enzymatic labels, filter sets to detect fluorescent labels, appropriate secondary labels such as a sheep anti-mouse-HRP, or the like). A kit may additionally include buffers and other reagents recognized for use in a method of the disclosure.

Having now generally provided the disclosure, the same will be more readily understood through reference to the following examples which are provided by way of illustration, and are not intended to be limiting of the disclosure, unless specified.

EXAMPLES

Example 1

Materials and Methods

Seventy-five (44 metastatic, 31 primary) formalin-fixed, paraffin-embedded neuroendocrine tumor samples were selected after 2-institution pathologist adjudication. The samples included subtypes gastrointestinal (n=12), pulmonary (n=22), Merkel cell (n=10), pancreatic (n=10), pheochromocytoma (n=10), and medullary thyroid carcinoma (n=11).

The following tumors were considered to have neuroendocrine differentiation: Merkel cell carcinoma, medullary thyroid carcinoma, pheochromocytoma, paraganglioma, pulmonary NEC (carcinoid, small cell carcinoma, large cell NEC), pancreatic NEC (all grades), and gastrointestinal NEC (all grades; stomach, small intestine, appendix, and colorectum). Both primary and metastatic cases were included. Excluded were some sites of "epithelial" neuroendocrine tumors (thymus, pituitary, kidney, bladder, cervix, ovary), carcinomas with occult/mixed neuroendocrine differentiation, and most of the rarer "neural" types of neuroendocrine tumors (neuroblastoma, olfactory neuroblastoma, central nervous system primitive neuroectodermal tumors).

Each case had been reviewed for diagnostic accuracy by consensus of two pathologists at different institutions. Case adjudication was performed by a primary pathologist through evaluation of clinical glass slides and available medical records, and by a second pathologist who viewed a selected slide(s) by online whole slide digital imaging (Spectrum™ and ImageScope, Aperio Technologies, Inc., Vista, Calif.) with clinicopathologic information provided by the originating pathologist. Only adjudicated cases in which pathologists at both institutions agreed upon a consensus diagnosis for tumor type and subtype were included in the study. Cases were graded according to the grading criteria for each subtype as outlined in Klimstra et al. and Hochwald et al. using mitotic rate and tumor necrosis as applicable. Merkel cell carcinomas were considered grade 3. Grade 1 and 2 tumors were considered to be well-differentiated tumors, while grade 3 tumors were considered to be poorlydifferentiated. Medullary carcinomas and pheochromocytomas/paragangliomas were not graded.

A summary of the samples is shown in Table 4.

TABLE 4

| Case Characteristics | | | | | | | |
|---|---|---|---|---|---|---|---|
| | | Sample | | Tumor Grade (of 3) | | | |
| | n | Primary | Metastatic | n/a | 1 | 2 | 3 |
| Gastrointestinal | 12 | 1 | 11 | 0 | 8 | 4 | 0 |
| Merkel cell | 10 | 7 | 3 | 0 | 0 | 0 | 10 |
| Pancreatic | 10 | 4 | 6 | 0 | 2 | 6 | 2 |
| Pheo/paraganglioma | 10 | 5 | 5 | 10 | 0 | 0 | 0 |
| Pulmonary | 22 | 14 | 8 | 0 | 11 | 0 | 11 |
| Thyroid medullary | 11 | 0 | 11 | 10 | 0 | 0 | 0 |
| Total | 75 | 31 (41%) | 44 (59%) | 20 (27%) | 21 (28%) | 10 (13%) | 23 (31%) |

Example 2

Classification of Neuroendocrine Tumors

Blinded samples were tested by the CancerType ID® 92-gene classifier (bioTheranostics, Inc), which makes tumor type predictions based upon quantitative PCR expression measurement for 87 gene targets and 5 reference genes. Briefly, a selected formalin fixed, paraffin embedded block was sectioned in RNase free conditions to produce one hematoxylin and eosin stained section and three unstained 7-micron sections for molecular testing. The freshly prepared slides included only a research ID. Samples were macrodissected using the H&E stained template or laser capture microdissected for tumor enrichment. Total RNA was extracted and DNase treated.

First strand cDNA was synthesized and then was pre-amplified (PreAmp, Life Technologies, Carlsbad, Calif.). Real-time PCR was then performed using an ABI 7900HT instrument quantitatively measuring the expression of 87 tumor-associated genes and 5 reference genes as previously described (Ma et al. 2006 "Molecular classification of human cancers using a 92-gene real-time quantitative polymerase chain reaction assay." *Arch Pathol Lab Med.* 130(4): 465-473). Comparison of the raw quantitative data was compared to a reference set of tumors (including all tumor types and subtypes predicted by the classifier) for prediction of neuroendocrine tumor type and subtype by a proprietary statistical algorithm.

Neuroendocrine tumor types and subtypes predicted by the 92-gene assay are adrenal-pheochromocytoma/paraganglioma, Neuroendocrine-skin (Merkel cell carcinoma), Neuroendocrine-lung-low-grade (pulmonary carcinoid), Neuroendocrine-lung-small cell/large cell (pulmonary small cell carcinoma or large cell neuroendocrine carcinoma), Neuroendocrine-intestine (neuroendocrine tumors of all grades from the alimentary tract), Neuroendocrine-pancreas (pancreatic endocrine tumors), and Thyroid-medullary (medullary thyroid carcinoma).

To select a gene subset for typing of neuroendocrine tumors, receiver operating characteristic (ROC) analysis was performed for each of the 87 tumor-associated genes using 2094 tumors from the 92-gene assay reference database to assess their discriminatory power to differentiate neuroendocrine tumors (N=290) from nonneuroendocrine tumors (N=1804). Genes with the highest area under curve (AUC) were chosen, and their performance in 957 cases from a blinded validation study was examined.

To identify a gene subset for subtyping neuroendocrine tumors, analysis of variance (ANOVA) was conducted for each of 87 genes using the 290 neuroendocrine tumors in the reference set. Genes with smallest P values were the ones that best distinguish the subtypes of neuroendocrine tumors and were thus selected as candidates for subtyping. The performance of the selected genes in the 75 neuroendocrine tumors from the validation study cohort was assessed by principal component analysis (PCA) and visualized in a 3-dimensional plot using the first three principal components to examine the separation of different neuroendocrine subtypes.

Example 3

Characteristics of Classification

All 75 neuroendocrine tumors met quality control parameters and were classified by the assay. The cohort included 44 females and 31 males, with a mean age of 62 years (range 29 to 86). Tumor characteristics are provided in Table 4. Cases were comprised of 59% metastatic tumors and 41% primary tumors. The most common biopsy site was liver, followed by lung and lymph node (FIG. 1). The performance characteristics for the 92-gene assay predictions of neuroendocrine subtype are shown in Table 5.

TABLE 5

| Neuroendocrine subtype | n | Matches | Sens | Spec | PPV | NPV |
|---|---|---|---|---|---|---|
| Gastrointestinal | 12 | 12 | 1.00 | 1.00 | 1.00 | 1.00 |
| Merkel cell | 10 | 10 | 1.00 | 0.97 | 0.83 | 1.00 |
| Pancreatic | 10 | 8 | 0.80 | 0.98 | 0.91 | 0.97 |
| Pheo/paraganglioma | 10 | 10 | 1.00 | 1.00 | 1.00 | 1.00 |
| Pulmonary | 22 | 20 | 0.91 | 1.00 | 1.00 | 0.98 |
| Thyroid Medullary | 11 | 11 | 1.00 | 1.00 | 1.00 | 1.00 |
| Total | 75 | 71 | 0.95 | | | |

Assay sensitivities were 99% (95% CI: 0.93-0.99) for accurate classification of neuroendocrine tumors and 95% (95% CI:0.87-0.98) for identification of tumor subtype for site of origin. Positive predictive values ranged from 0.83 to 1.00 for individual subtypes. A confusion matrix comparing the reference diagnosis with the 92-assay results is shown in Table 6; this highlights areas of concordance and discordance between the 92-gene classifier subtyped cases and reference diagnosis.

TABLE 6

| | Neuroendocrine subtype | Germ cell non-seminoma | Neuroendocrine-intestine | Neuroendocrine-skin | Neuroendocrine-pancreas | Adrenal-pheo | Neuroendocrine-lung-low-grade | Neuroendocrine-lung-small/large cell | Thyroid-medullary | Grand Total |
|---|---|---|---|---|---|---|---|---|---|---|
| Reference diagnosis | Gastrointestinal | | 12 | | | | | | | 12 |
| | Merkel cell | | | 10 | | | | | | 10 |
| | Pancreatic | 1 | | 1 | 8 | | | | | 10 |
| | Pheo/paraganglioma | | | | | 10 | | | | 10 |
| | Pulmonary carcinoid | | | | 1 | | 10 | | | 11 |
| | Pulmonary high-grade | | | 1 | | | | 10 | | 11 |
| | Thyroid Medullary | | | | | | | | 11 | 11 |
| | Grand Total | 1 | 12 | 12 | 9 | 10 | 10 | 10 | 11 | 75 |

92-gene assay

The concordance rate of the molecular results with the reference diagnoses in poorly differentiated NEC (grade 3 tumors) was 87% (20/23), whereas for well-differentiated NEC (grade 1 and 2 tumors from the GI tract, pancreas, or lung) it was 97% (30/31).

Four cases had discordant 92-gene assay predictions compared to the reference diagnosis. Three of the four cases were correctly predicted as neuroendocrine carcinoma, but were discordant at the subtype (site of origin) level. Case 1 was adjudicated as an endobronchial pulmonary well-differentiated neuroendocrine (carcinoid) tumor with liver metastases at the time of primary diagnosis that was predicted by the assay to be a pancreatic endocrine primary. Case 2 was a pulmonary small cell carcinoma predicted to be Merkel cell carcinoma. Case 3 was a poorly differentiated pancreatic NEC predicted to be a Merkel cell carcinoma. Case 4 was adjudicated as a poorly differentiated pancreatic NEC and predicted to be a nonseminomatous germ cell tumor, however, a neuroendocrine tumor type was not ruled out by the assay (data not shown).

Example 4

Analysis of Neuroendocrine Gene Subsets

Figure 2B:
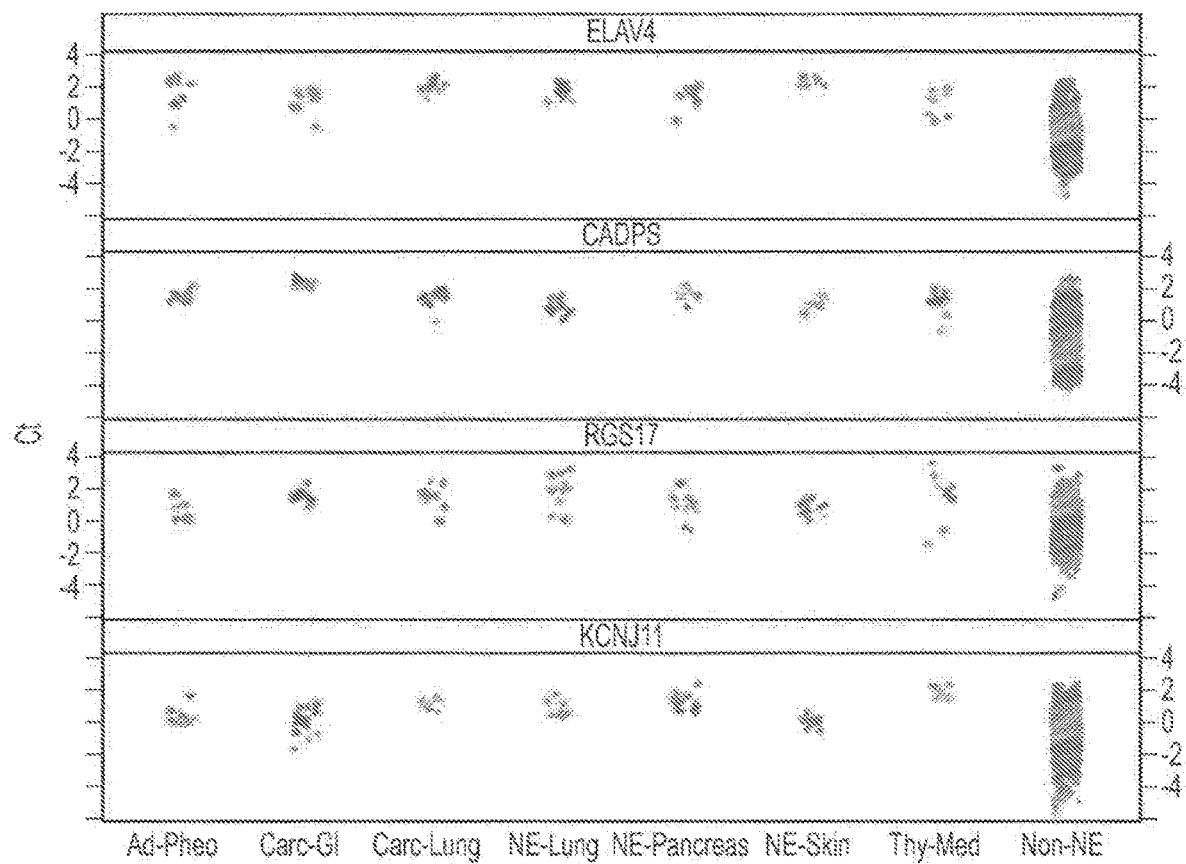
FIG. 2, part (A) provides the gene symbol, alternate names, chromosome location, and proposed/known function for four (4) genes differentially expressed in neuroendocrine (NE) tumors versus other tumor types. Part (B) shows stripchart plots of four selected genes with AUC higher than 0.8. The plots are showing the distribution of $C_T$ values of each gene in each subtype of NE cases as well as in Non-NE cases in the validation cohort.

Further analysis was explored to potentially define a smaller subset of genes within the 92-gene assay panel with high sensitivities and specificities for neuroendocrine classification and subtyping. Four genes demonstrated high discriminatory ability for distinguishing neuroendocrine from non-neuroendocrine tumor types in the assay reference set (N=2094), based on an AUC cutoff of ≥0.8 from the ROC analysis. Consistently, AUC values for these 4 genes were >0.8 in the 957 cases from the validation study cohort (FIG. 2A). Biomarker utility for discrimination of neuroendocrine from non-neuroendocrine tumors can also be seen in the stripchart plots showing the distribution of expression values of each gene in each of the subtypes of neuroendocrine cases, as well as in non-neuroendocrine cases in the validation cohort (FIG. 2B).

The top 15 genes with significant P values from ANOVA analysis were selected as candidate genes to best distinguish different subtypes of neuroendocrine tumors in the reference set. These genes are described in Table 2 and include KIF2C, SFTA3, CDCA3, KIF12, CDH17, LOC100130899 (uncharacterized), NBLA00301, HOXD11, EPS8L3, IRX3, WWC1, HOXB8, FOXG1, BCL11B, and LOC100506088 (uncharacterized).

Figure 3:
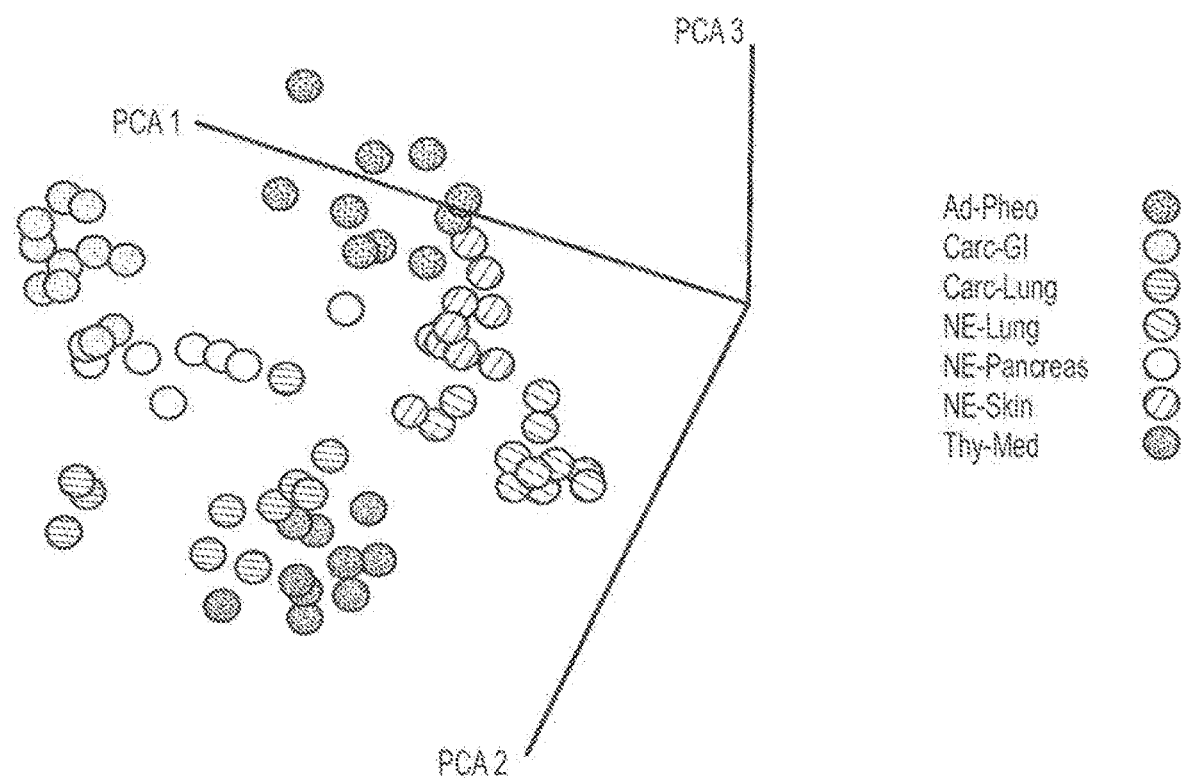
FIG. 3 is a 3-dimensional principle component analysis (PCA) plot shows the clustering pattern of the cases of different neuroendocrine tumor subtypes.
Figure 4A:
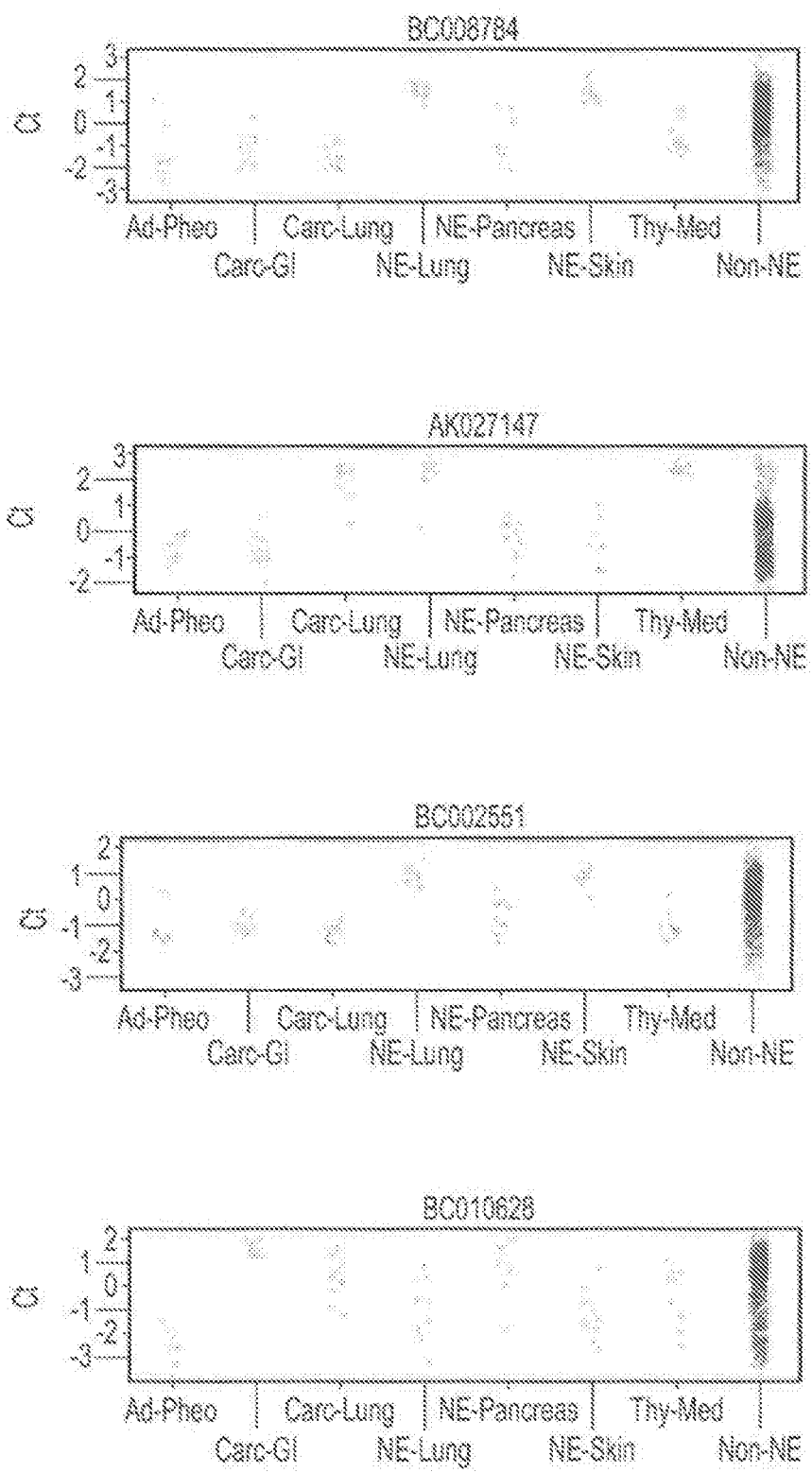
FIGS. 4A through 4D show stripchart plots of 15 disclosed genes and the distribution of $C_T$ values of each gene in each subtype of neuroendocrine (NE) cases as well as in Non-NE cases. Ad-Pheo is adrenal-pheochromocytoma/paraganglioma, Carc-GI is neuroendocrine-intestine, Carc-Lung is lung-low-grade or pulmonary carcinoid, NE-Lung is neuroendocrine-lung-small cell or lung-large cell carcinoma, NE-Pancreas is pancreatic neuroendocrine tumor, NE-Skin is Merkel cell carcinoma, and Thy-Med is medullary thyroid carcinoma.
Figure 4B:
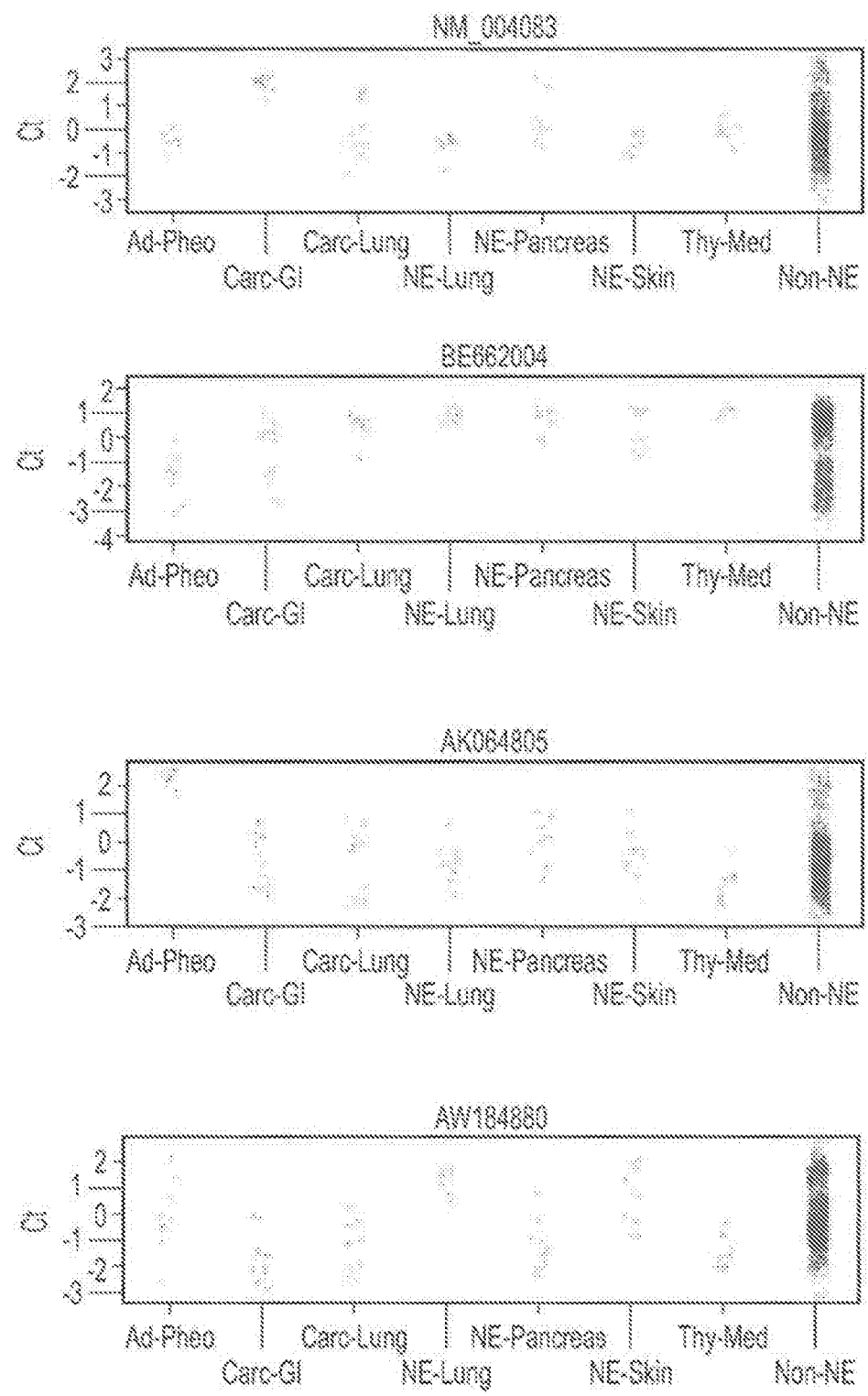
Figure 4C:
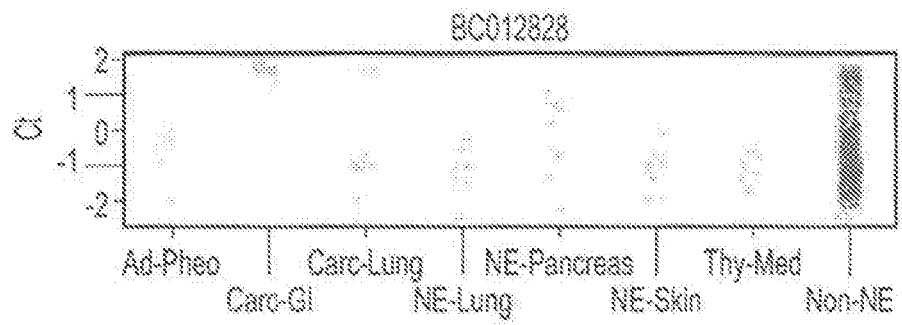
Figure 4C:
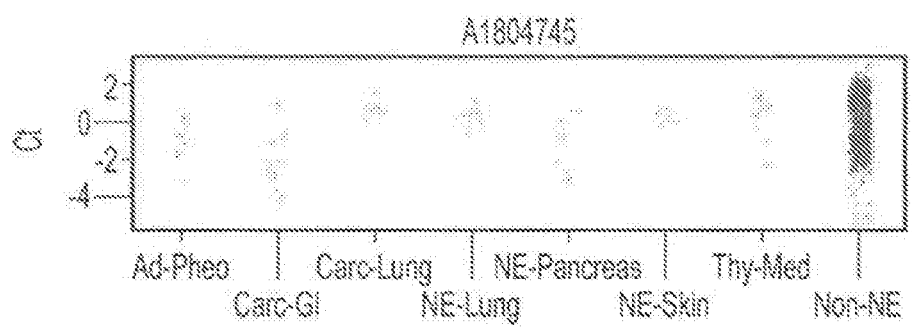
Figure 4C:
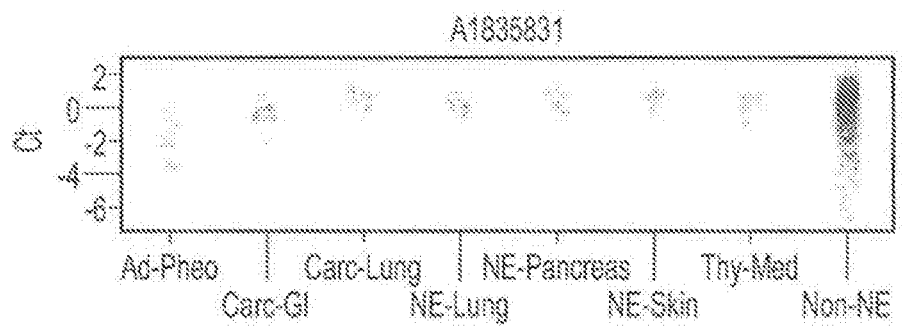
Figure 4C:
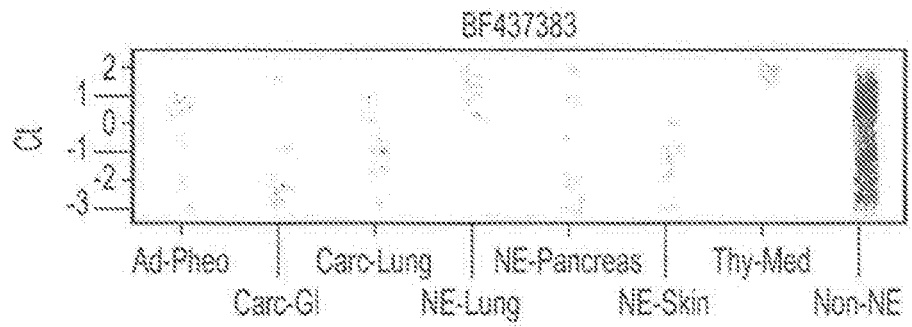
Figure 4D:
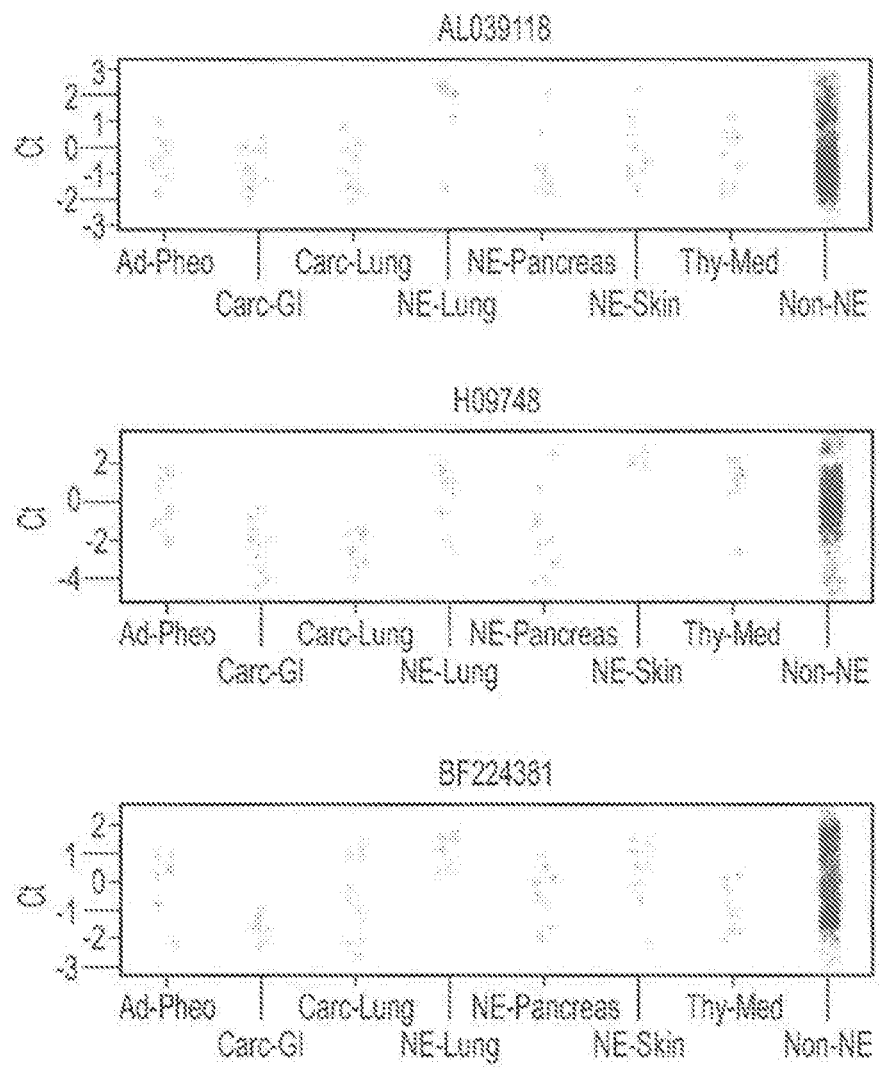

To visualize how well these 15 genes can distinguish neuroendocrine subtypes in the validation cohort, PCA were performed and the first 3 principal components were used to produce a 3-dimensional plot showing the unsupervised clustering pattern of the different neuroendocrine subtypes (FIG. 3). The PCA plot shows distinct separation of each neuroendocrine subtype, and provides preliminary evidence that neuroendocrine subtyping may be feasible through optimization of the collective expression of the 15-gene set.

Example 5

Performance

The 97% accuracy of the 92-gene assay for well-differentiated neuroendocrine tumors reported here is superior to published findings using IHC panels. All well differentiated neuroendocrine tumors from the GI tract (12/12) and pancreas (8/8) and 91% (10/11) of pulmonary well-differentiated neuroendocrine tumors were correctly classified for site of origin in our study; this included both metastatic and primary tumors. Correct identification of primary site in the metastatic setting is important, as treatment options and prognosis differ for thoracic, pancreatic and gastrointestinal tract based neuroendocrine tumors. Sangoi et al. showed that IHC for PAX8 had only a 65% sensitivity for identifying pancreatic origin in well-differentiated neuroendocrine tumors metastatic to the liver. Several cases of primary gastrointestinal neuroendocrine tumors in this study expressed PAX8. Long et al.66 found similar results, with positive staining for PAX8 in only 50% of pancreatic neuroendocrine tumors metastatic to the liver, and with positive staining of all duodenal, 85% of rectal and approximately 20% of appendiceal and gastric primary neuroendocrine tumors.

In this study, the only gastrointestinal tumors metastatic to the liver that were tested for PAX8 were ileal tumors, which never showed any positive staining for PAX8 in the primary tumors. Srivastava et al. demonstrated that an IHC panel including CDX2, PDX-1, NESP-55, and TTF-1 had limited performance for accurately predicting the primary site of gastrointestinal and pulmonary primary tumors although it showed a sensitivity and specificity of 97% and 91% for predicting pancreatic origin. In poorly differentiated tumors, the 92-gene assay showed rare discordant cases, but even in these diagnostically challenging cases the assay displayed an excellent overall performance overall of 87%.

The strength of molecular diagnostics, including the 92-gene assay, for tumor classification lies both in standardized testing methods and in the comparison of gene expression between tumor samples and a well-adjudicated and robust expression database. Real-time, quantitative PCR for measurement of RNA expression is a standardized, highly reproducible, multiplexed panel of expression markers, but with a logarithmically extended dynamic range of gene expression measurement superior to protein IHC.

Because the signals are not directly visualized on tumor tissue, however, this assay may be optionally used with careful guidance by a pathologist to ensure sample selection for enrichment of tumor and exclusion of interfering normal cells (lymphocytes, fibroblasts, etc.), a process of which is already growing rapidly within laboratories performing molecular oncology testing.

Fifteen (15) genes were identified that showed reasonable discrimination between neuroendocrine tumors from different anatomic sites in this set of tested tumor samples. Because their initial discovery was part of a data-driven process looking at differential gene expression across a diverse and wide variety of tumor types, and not for neuroendocrine typing in particular, mechanistic links to neuroendocrine differentiation or specific neuroendocrine tumor types are currently unknown, and so they may reflect an unexpected discovery.

All references cited herein, including patents, patent applications, and publications, are hereby incorporated by reference in their entireties, whether previously specifically incorporated or not.

Having now fully described the inventive subject matter, it will be appreciated by those skilled in the art that the same can be performed within a wide range of equivalent parameters, concentrations, and conditions without departing from the spirit and scope of the disclosure and without undue experimentation.

While this disclosure has been described in connection with specific embodiments thereof, it will be understood that it is capable of further modifications. This application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth.

What is claimed is:

1. A method for treating a pancreatic neuroendocrine tumor in a subject, the method comprising
   determining mRNA expression levels of four sequences consisting of ELAVL4, CADPS, RGS17 and KCNJ11 in a sample obtained from the subject;
   comparing the ELAVL4, CADPS, RGS17 and KCNJ11 expression levels to expression levels of ELAVL4, CADPS, RGS17 and KCNJ11 in a known reference specimen, wherein the known reference specimen is a known pancreatic neuroendocrine tumor;
   classifying the sample as containing pancreatic neuroendocrine tumor cells based on detecting ELAVL4, CADPS, RGS17 and KCNJ11 expression levels that are positively correlated to the expression levels of ELAVL4, CADPS, RGS17 and KCNJ11 in the known reference specimen; and
   administering a tyrosine kinase inhibitor or mTOR inhibitor to the subject after the sample has been classified as containing pancreatic neuroendocrine tumor cells.

2. The method of claim 1, wherein the determining comprises detection of cDNA copies of the mRNA.

3. The method of claim 2, wherein the determining comprises amplifying the cDNA copies.

4. The method of claim 2, wherein the detection comprises sequencing the cDNA copies.

5. The method of claim 1, wherein the determining comprises labeling the mRNA.

6. The method of claim 3, wherein the amplifying comprises amplification of all or part of the sequences, or reverse transcription and labeling mRNA corresponding to the sequences.

7. The method of claim 6, wherein the amplification comprises linear RNA amplification or quantitative PCR.

8. The method of claim 6, wherein the amplification is quantitative PCR amplification of at least 50 nucleotides of the sequences.

9. The method of claim 1, wherein the sample is a formalin fixed, paraffin embedded (FFPE) sample.

10. The method of claim 1, wherein the sample is from lymph nodes of the subject.

* * * * *

SEQUENCE LISTING

```
<160> NUMBER OF SEQ ID NOS: 19

<210> SEQ ID NO 1
<211> LENGTH: 60
<212> TYPE: DNA
<213> ORGANISM: Homo sapiens

<400> SEQUENCE: 1
ggagggaggg ctaattatat attttgttgt tcctctatac tttgttctgt tgtctgcgcc      60

<210> SEQ ID NO 2
<211> LENGTH: 60
<212> TYPE: DNA
<213> ORGANISM: Homo sapiens

<400> SEQUENCE: 2
ttctcttttg ggggcaaaca ctatgtcctt ttcttttct agatacagtt aattcctgga       60

<210> SEQ ID NO 3
<211> LENGTH: 60
<212> TYPE: DNA
<213> ORGANISM: Homo sapiens

<400> SEQUENCE: 3
agtgttgcaa gtttccttta aaaccaacaa agcccacaag tcctgaattt cccattctta     60

<210> SEQ ID NO 4
<211> LENGTH: 60
<212> TYPE: DNA
<213> ORGANISM: Homo sapiens

<400> SEQUENCE: 4
tctgtaactg cacaaccctg gggtttgctg cagagctatt tctttccatg taaagtagtg     60

<210> SEQ ID NO 5
<211> LENGTH: 60
<212> TYPE: DNA
<213> ORGANISM: Homo sapiens

<400> SEQUENCE: 5
```

```
ttgtaatcat gccaattcca gatcaataac tgcatgtctg ttctttggta gaaatagctt    60
```

\<210\> SEQ ID NO 6
\<211\> LENGTH: 60
\<212\> TYPE: DNA
\<213\> ORGANISM: Homo sapiens

\<400\> SEQUENCE: 6

```
ttcatttcca aacatcatct ttaagactcc aaggattttt ccaggcacag tggctcatac    60
```

\<210\> SEQ ID NO 7
\<211\> LENGTH: 60
\<212\> TYPE: DNA
\<213\> ORGANISM: Homo sapiens

\<400\> SEQUENCE: 7

```
gggtggagtt tcagtgagaa taaacgtgtc tgcctttgtg tgtgtgtata tatacagaga    60
```

\<210\> SEQ ID NO 8
\<211\> LENGTH: 60
\<212\> TYPE: DNA
\<213\> ORGANISM: Homo sapiens

\<400\> SEQUENCE: 8

```
ctttgggccg agcactgaat gtcttgtact ttaaaaaaat gtttctgaga cctctttcta    60
```

\<210\> SEQ ID NO 9
\<211\> LENGTH: 60
\<212\> TYPE: DNA
\<213\> ORGANISM: Homo sapiens

\<400\> SEQUENCE: 9

```
ctggacccett ggagcagtgt tgtgtgaact tgcctagaac tctgccttct ccgttgtcaa    60
```

\<210\> SEQ ID NO 10
\<211\> LENGTH: 60
\<212\> TYPE: DNA
\<213\> ORGANISM: Homo sapiens

\<400\> SEQUENCE: 10

```
tccttcctct tcggtgaatg caggttattt aaactttggg aaatgtactt ttagtctgtc    60
```

\<210\> SEQ ID NO 11
\<211\> LENGTH: 60
\<212\> TYPE: DNA
\<213\> ORGANISM: Homo sapiens

\<400\> SEQUENCE: 11

```
ctcagactgg gctccacact cttgggcttc agtctgccca tctgctgaat ggagacagca    60
```

\<210\> SEQ ID NO 12
\<211\> LENGTH: 60
\<212\> TYPE: DNA
\<213\> ORGANISM: Homo sapiens

\<400\> SEQUENCE: 12

```
cctaatgggg attcctctgg ttgttcactg ccaaaactgt ggcatttttca ttacaggaga    60
```

\<210\> SEQ ID NO 13
\<211\> LENGTH: 60
\<212\> TYPE: DNA
\<213\> ORGANISM: Homo sapiens

\<400\> SEQUENCE: 13

```
gccatgcata catgctgcgc atgttttctt cattcgtatg ttagtaaagt tttggttatt    60

<210> SEQ ID NO 14
<211> LENGTH: 60
<212> TYPE: DNA
<213> ORGANISM: Homo sapiens

<400> SEQUENCE: 14
cacctattta ttttacctct ttcccaaacc tggagcattt atgcctaggc ttgtcaagaa    60

<210> SEQ ID NO 15
<211> LENGTH: 60
<212> TYPE: DNA
<213> ORGANISM: Homo sapiens

<400> SEQUENCE: 15
aattctctat aaacggttca ccagcaaacc accaatacat tccattgttt gcctagagag    60

<210> SEQ ID NO 16
<211> LENGTH: 60
<212> TYPE: DNA
<213> ORGANISM: Homo sapiens

<400> SEQUENCE: 16
tgagttcagc atgtgtctgt ccatttcatt tgtacgcttg ttcaaaacca agtttgttct    60

<210> SEQ ID NO 17
<211> LENGTH: 60
<212> TYPE: DNA
<213> ORGANISM: Homo sapiens

<400> SEQUENCE: 17
taccaaactg ggactcacag ctttattggg ctttctttgt gtcttgtgtg tttcttttat    60

<210> SEQ ID NO 18
<211> LENGTH: 60
<212> TYPE: DNA
<213> ORGANISM: Homo sapiens

<400> SEQUENCE: 18
ttgtcttaaa atttcttgat tgtgatactg tggtcatatg cccgtgtttg tcacttacaa    60

<210> SEQ ID NO 19
<211> LENGTH: 60
<212> TYPE: DNA
<213> ORGANISM: Homo sapiens

<400> SEQUENCE: 19
ttgtgcaaaa gtcccacaac ctttctggat tgatagtttg tggtgaaata aacaatttta    60
```